US008232373B2

(12) United States Patent
Wang

(10) Patent No.: US 8,232,373 B2
(45) Date of Patent: Jul. 31, 2012

(54) IMMUNOGENIC PEPTIDE COMPOSITION FOR THE PREVENTION AND TREATMENT OF ALZHEIMER'S DISEASE

(75) Inventor: Chang Yi Wang, Cold Spring Harbor, NY (US)

(73) Assignee: United Biomedical, Inc., Hauppauge, NY (US)

( * ) Notice: Subject to any disclaimer, the term of this patent is extended or adjusted under 35 U.S.C. 154(b) by 0 days.

(21) Appl. No.: 12/960,125

(22) Filed: Dec. 3, 2010

(65) Prior Publication Data

US 2011/0070255 A1 Mar. 24, 2011

Related U.S. Application Data

(62) Division of application No. 10/861,614, filed on Jun. 4, 2004, which is a division of application No. 09/865,294, filed on May 25, 2001, now Pat. No. 6,906,169.

(51) Int. Cl.
*C12P 21/02* (2006.01)
*C07K 2/00* (2006.01)
*C07K 1/04* (2006.01)

(52) U.S. Cl. .................... 530/403; 536/23.4; 424/185.1; 435/69.7

(58) Field of Classification Search ........................ None
See application file for complete search history.

(56) References Cited

U.S. PATENT DOCUMENTS

| | | | | |
|---|---|---|---|---|
| 5,750,349 | A | 5/1998 | Suzuki et al. | |
| 5,753,624 | A | 5/1998 | McMichael | |
| 5,759,551 | A * | 6/1998 | Ladd et al. | 424/198.1 |
| 5,843,446 | A | 12/1998 | Ladd et al. | |
| 5,955,317 | A | 9/1999 | Suzuki et al. | |
| 6,025,468 | A | 2/2000 | Wang | |
| 6,228,987 | B1 | 5/2001 | Wang | |
| 6,750,324 | B1 | 6/2004 | Schenk et al. | |
| 6,787,138 | B1 | 9/2004 | Schenk | |
| 6,906,169 | B2 | 6/2005 | Wang | |
| 2003/0165481 | A1* | 9/2003 | Hersh | 424/93.21 |
| 2006/0088548 | A1 | 4/2006 | Chain | |

FOREIGN PATENT DOCUMENTS

| | | |
|---|---|---|
| EP | 0 526 511 B1 | 5/1997 |
| WO | WO 94/28412 | 12/1994 |
| WO | WO 95/11998 | 5/1995 |
| WO | WO 99/27944 | 6/1999 |
| WO | WO 99/66952 | 12/1999 |
| WO | WO 99/66957 | 12/1999 |
| WO | WO 00/72880 | 12/2000 |
| WO | WO 01/18169 | 3/2001 |
| WO | WO 01/42306 | 6/2001 |

OTHER PUBLICATIONS

Wong et al. PNAS, 82:8729-8732, 1985.*

Behrouz, N., et al. Antiserum to the N-Terminal Subsequence of the Alzheimer Amyloid Beta Protein Does Not React With Neurofibrillary Tangles. *Journal Gerontology*. 1998, vol. 44, No. 6, pp. B156-B159.

Hanan, E., et al. Inhibitory Effect of Monoclonal Antibodies on Alzheimer's Beta-Amylod Peptide Aggregation. *Int. J. Exp. Clin. Invest*. 1996, vol. 3, pp. 130-133.

Majocha, R.E., et al. Development of a Monoclonal Antibody Specific for Beta/A4 Amyloid in Alzheimer's Disease Brain for Application in in Vivo Imaging of Amyloid Angiopathy. *J. Nuc. Med*. Dec. 1992, vol. 33, No. 12, pp. 2184-2189.

Solomon, B., et al. The Amino Terminus of Beta-Amyloid Peptide Contains an Essential Epitope for Maintaining its Solubility. *Progress in Alzheimer's and Parkinson's Diseases*. Ed. by Fisher et al., Plenum Press, (New York, NY), 1998, pp. 205-211.

Jobling, et al. Analysis of Structure and Function of the B Subunit of Cholera Toxin by the Use of Site-Directed Mutagenesis. *Mol. Microbiol*., 1991, 5(7):1755-1767.

Kumar, et al. In Vitro Cellular & Developmental Biology—Animal. *Springer*. (Berlin / Heidelberg), vol. 36, No. 2, Feb. 2000, pp. 81-87.

International Search Report as issued in related International Application No. PCT/US02/10293, dated Sep. 30, 2004.

European Search Report as issued in related European Application No. 02731223, dated Jun. 27, 2005.

Supplemental European Search Report as issued in related European Application No. 02731223, dated Oct. 4, 2005.

European Search Report as issued in related European Application No. 09168110.6, dated Oct. 6, 2009.

Anderton, "Progress in molecular pathology", *Nature*, 1987; 325:658-659.

Araujo and Cotman, "β-Amyloid stimulates glial cells in vitro to produce growth factors that accumulate in senile plaques in Alzheimer's disease", *Brain Res*., 1992; 569:141-145. Arispe et al., "Alzheimer disease amyloid βprotein forms calcium channels in bilayer membranes: Blockade by tromethamine and aluminum", *Proc. Natl. Acad. Sci. USA*, 1993; 90:567-571.

Babbitt et al., "Binding of immunogenic peptides to Ia histocompatibility molecules", *Nature*, 1985; 317:359.

Bard et al., "Peripherally administered antibodies against amyloid β-peptide enter the central nervous system and reduce pathology in a mouse model of Alzheimer disease", *Nature Medicine*, 2000; 6:916-919.

Barnes, "Defect in Alzheimer's is on Chromosome 21", *Science*, 1987; 235:846-847.

(Continued)

*Primary Examiner* — Daniel E Kolker
*Assistant Examiner* — Stacey MacFarlane
(74) *Attorney, Agent, or Firm* — Locke Lord LLP

(57) ABSTRACT

The present invention relates to a composition comprising a peptide immunogen useful for the prevention and treatment of Alzheimer's Disease. More particularly, the peptide immunogen comprises a main functional/regulatory site, an N-terminal fragment of Amyloid β (Aβ) peptide linked to a helper T cell epitope (Th) having multiple class II MHC binding motifs. The peptide immunogen elicits a site-directed immune response against the main functional/regulatory site of the Aβ peptide and generate antibodies, which are highly cross-reactive to the soluble $A\beta_{1-42}$ peptide and the amyloid plaques formed in the brain of Alzheimer's Disease patients. The antibodies elicited being cross reactive to the soluble $A\beta_{1-42}$ peptide, promote fibril disaggregation and inhibit fibrillar aggregation leading to immunoneutralization of the "soluble Aβ-derived toxins"; and being cross-reactive to the amyloid plaques, accelerate the clearance of these plaques from the brain. Thus, the composition of the invention comprising the peptide immunogen is useful for the prevention and treatment of Alzheimer's Disease.

10 Claims, 2 Drawing Sheets

OTHER PUBLICATIONS

Behl et al., "Hydrogen Peroxide Mediates Amyloid βProtein Toxicity", *Cell*, 1994; 77:817-827.

Busciglio et al., "β-Amyloid Fibrils Induce Tau Phosphorylation and Loss of Microtubule Binding", *Neuron*, 1995; 14:879-888.

Cease et al., "Helper T-cell antigenic site identification in the acquired immunodeficiency syndrome virus gp120 envelope protein and induction of immunity in mice to the native protein using a 16-residue synthetic peptide", *Proc. Natl. Acad. Sci. USA*, 1987; 84:4249-4253.

Chapman, "Model behaviour—Trials in mice of a possible vaccine for Alzheimer's disease show that it reduces the behavioural defects and the brain damage seen in the desease. As promising as these results are, a human vaccine remains a long way off", *Nature*, 1992; 408:915-916.

Citron et al, "Mutation of the β-amyloid precursor protein in familial Alzheimer's disease increases β-protein production", *Nature*, 1992; 360:672-674.

Eldridge et al., "Biodegradable Microspheres as a vaccine delivery system", *Molec. Immunol.*, 1991; 28-287-294.

Ferrari et al, *J.* "Identification of Immunodominant T Cell Epitopes of the Hepatitis B Virus Nucleocapsid Antigen", *Clin. Invest.*, 1991; 88:214-222.

Fields et al., "Principles and Practice of Solid-Phase Peptide Synthesis", *Synthetic Peptides: A User's Guide*, Chapter 3, 1992:77-183.

Frenkel et al., "Immunization against Alzheimer's β-amyloid plaques via EFRH phage administration", *Proc. Natl. Acad. Sci. USA*, 2000; 97:11455-11459.

Frenkel et al., "Generation of auto-antibodies towards Alzheimer's disease vaccination", *Vaccine*, 2001; 19:2615-2619.

Gaskin et al., "Autoantibodies to Neurofibrillary Tangles and Brain Tissue in Alzheimer's Disease", *JEM*, 1987; 165:245.

Glenner and Wong, "Alzheimer's Disease: Initial Report of the Purification and Characterization of a Novel Cerebrovascular Amyloid Protein", *Biochem Biophys Res Comm*, 1984; 120-885-890.

Glenner and Wong, "Alzheimer's Disease and Down's Syndrome: Sharing of a Unique Cerebrovascular Amyloid Fibril Protein", *Biochem Biophys Res Comm*, 1984; 122:1131-1135.

Goate et al., "Segregation of a missense mutation in the amyloid precursor protein gene with familial Alzheimer's disease", *Nature*, 1991; 349:704-706.

Grubeck-Loebenstein et al., "Immunization with beta-amyloid: could T-cell activation have a harmful effect?", *Trends in Neuroscience*, 2000; 23:114.

Janus et al., "Aβ Peptide Immunization Reduces Behavioural Impairment and Plaques in a Model of Alzheimer's Disease", *Nature*, 2000; 408:979-982.

Johnson-Wood et al., "Amyloid Precursor Protein Processing and $A\beta_{42}$ Deposition in a Transgenic Mouse Model of Alzheimer Disease", *Proc. Natl. Acad. Sci.* USA, 1997; 94:1550-1555.

Kang et al., "The precursor of Alzheimer's Disease Amyloid A4 protein Resembles a Cell-Surface Receptor", *Nature*, 1987; 325:733-737.

Klein et al., "Targeting Small Aβ Oligomers: The Solution to an Alzheimer's Disease Conundrum?", *Trends in Neurosciences*, 2001; 24:219-224.

Lemere et al., "Nasal Aβ Treatment Induces Anti-Aβ Antibody Production and Decreases Cerebral Amyloid Burden in PD-APP Mice", *Annals of the New York Academy of Sciences* 2000, 920:328-332.

Masters et al., "Amyloid Plaque Core Protein in Alzheimer Disease and Down Syndrome", *Proc. Natl. Acad. Sci.* USA, 1985; 82:4245-4249.

Meister et al., "Two Novel T Cell Epitope Prediction Algorithms Based on MHC-Binding Motifs; Comparison of Predicted and Published Epitopes from Mycrobacterium Tuberculosis and HIV Protein Sequences", *Vaccine*, 1995; 13:581-591.

Morgan et al., "Aβ Peptide Vaccination Prevents Memory Loss in an Animal Model of Alzheimer's Disease", *Nature*, 2000; 408:982-985.

Mullan et al., "A Pathogenic Mutation for Probable Alzheimer's Disease in the App Gene at the N-Terminus of β-amyloid", *Nature Genetics*, 1992; 1:345-347.

O'Hagan et al., "Controlled Release Microparticles for Vaccine Development", *Vaccine*, 1991; 9:768-771.

Partidos et al., "Immune Responses in Mice Following Immunization with Chimeric Synthetic Peptides Representing B and T Cell Epitopes of Measles Virus Proteins", *J. Gen. Virol.*, 1991; 72:1293.

Schenk et al., "Immunization with Amyloid-β Attenuates Alzheimer-disease-like Pathology in the PDAPP mouse", *Nature*, 1999; 400:173-177.

Schenk et al., "β-Peptide Immunization—A Possible New Treatment for Alzheimer Disease", *Archives of Neurology* 2000, 57:934-936.

Selkoe, "Amyloid β-Protein and the Genetics of Alzheimer's Disease", *J. Biol. Chem.*, 1996; 271:18295-18298.

Seubert et al., "Isolation and Quantification of Soluble Alzheimer's β-peptide from Biological Fluids", *Nature*, 1992; 359:325-327.

Soloman et al., "Monoclonal Antibodies Inhibit in Vitro Fibrillar Aggregation of the Alzheimer β-amyloid Peptide", *Proc. Natl. Acad. Sci.* USA, 1996; 93:452-455.

Soloman et al., "Disaggregation of Alzheimer β-amyloid by Site-Directed mAb", *Proc. Natl. Acad. Sci.* USA, 1997; 94:4109-4112.

Stagg et al., "Primary Human T-cell Responses to the Major Outer Membrane Protein of Chlamydia Trachomatis", *Immunology*, 1993; 79:1-9.

Terry et al., "The Neuropathology of Alzheimer Disease and the Structural Basis of its Cognitive Alterations", in *Alzheimer Disease*, 1999, 187-206.

Thomas et al., "β-Amyloid-mediated Vasoactivity and Vascular Endothelial Damage", *Nature*, 1996; 380:168-171.

Wang et al., "Long-Term High-Titer Neutralizing Activity Induced by Octameric Synthetic HIV-1 Antigen", *Science*, 1991; 254:285-288.

Yankner et al., "Neurotrophic and Neurotoxic Effects of Amyloid β Protein: Reversal by Tachykinin Neuropeptides", *Science*, 1990; 250:279-282.

Peet NM et al. "The effect of low-profile serine substitutions in the V3-loop of HIV-1 gp120 IIIB/LAI on the immunogenicity of the envelope protein." *Virology*, 1998; 251:59-70.

King TP et al. "Structure-immunogenicity relationship of melittin and its N-terminal truncated analogs." *Biochemistry*, 1993; 32:3506-3510.

Skolnick J et al. "From genes to protein structure and function: novel applications of computational approaches in the genomic era." *Trends in Biotech*, 2000; 18:34-39.

Su GC et al. "Intravascular infusions of soluble beta-amyloid compromise the blood-brain barrier, activate CNS glial cells and induce peripheral hemorrhage." *Brain Res*, 1999; 818:105-117.

de Lustig ES et al. "Peripheral markers and diagnostic criteria in Alzheimer's disease: Critical evaluations." *Rev in Neurosciences*, 1994; 5:213-224.

Munch G and Robinson R. "Potential neurotoxic inflammatory responses to Abeta vaccination in humans." *J. Neural Transm.*, 2002; 109:1081-1087.

Vickers JC. "A vaccine against Alzheimer's disease." *Drugs Aging.*, 2002; 19(7):487-494.

Young E. "Alzheimer's vaccine trial suspended." *New Scientist*, 2002; 14:50.

* cited by examiner

AD Brain 11

AD Brain 2

Figure 2
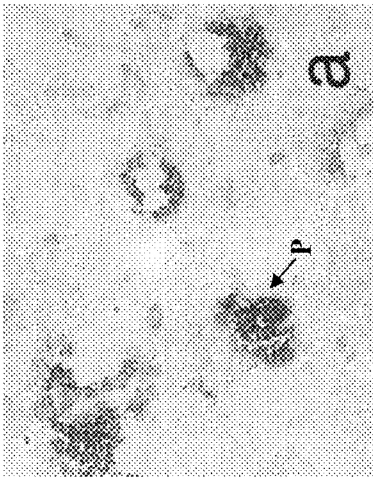
Fig. 2a
Fig. 2b
Fig. 2c
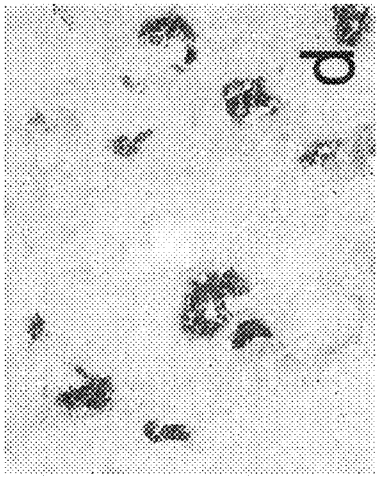
Fig. 2d
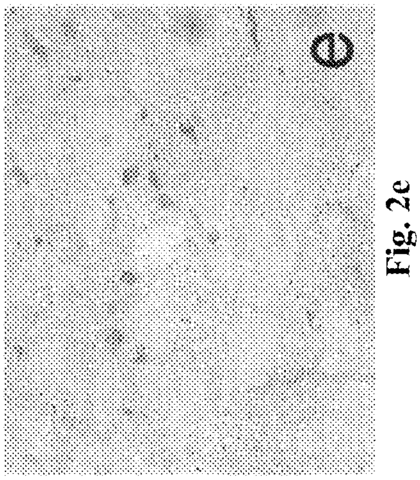
Fig. 2e

SEQUENCE LISTING

<160> NUMBER OF SEQ ID NOS: 77

<210> SEQ ID NO 1
<211> LENGTH: 15
<212> TYPE: PRT
<213> ORGANISM: Hepatitis B virus

<400> SEQUENCE: 1

```
Phe Phe Leu Leu Thr Arg Ile Leu Thr Ile Pro Gln Ser Leu Asp
1               5                   10                  15
```

<210> SEQ ID NO 2
<211> LENGTH: 30
<212> TYPE: PRT
<213> ORGANISM: Bordetella pertussis

<400> SEQUENCE: 2

```
Lys Lys Leu Arg Arg Leu Leu Tyr Met Ile Tyr Met Ser Gly Leu Ala
1               5                   10                  15

Val Arg Val His Val Ser Lys Glu Glu Gln Tyr Tyr Asp Tyr
            20                  25                  30
```

<210> SEQ ID NO 3
<211> LENGTH: 17
<212> TYPE: PRT
<213> ORGANISM: Clostridium tetani

<400> SEQUENCE: 3

```
Lys Lys Gln Tyr Ile Lys Ala Asn Ser Lys Phe Ile Gly Ile Thr Glu
1               5                   10                  15

Leu
```

<210> SEQ ID NO 4
<211> LENGTH: 22
<212> TYPE: PRT
<213> ORGANISM: Clostridium tetani

<400> SEQUENCE: 4

```
Lys Lys Phe Asn Asn Phe Thr Val Ser Phe Trp Leu Arg Val Pro Lys
1               5                   10                  15

Val Ser Ala Ser His Leu
            20
```

<210> SEQ ID NO 5
<211> LENGTH: 15
<212> TYPE: PRT
<213> ORGANISM: Bordetella pertussis

<400> SEQUENCE: 5

```
Tyr Met Ser Gly Leu Ala Val Arg Val His Val Ser Lys Glu Glu
1               5                   10                  15
```

<210> SEQ ID NO 6
<211> LENGTH: 27
<212> TYPE: PRT
<213> ORGANISM: Clostridium tetani

<400> SEQUENCE: 6

```
Tyr Asp Pro Asn Tyr Leu Arg Thr Asp Ser Asp Lys Asp Arg Phe Leu
1               5                   10                  15

Gln Thr Met Val Lys Leu Phe Asn Arg Ile Lys
            20                  25
```

<210> SEQ ID NO 7
<211> LENGTH: 24
<212> TYPE: PRT
<213> ORGANISM: Pertusaria trachythallina

<400> SEQUENCE: 7

Gly Ala Tyr Ala Arg Cys Pro Asn Gly Thr Arg Ala Leu Thr Val Ala
1 5 10 15

Glu Leu Arg Gly Asn Ala Glu Leu
20

<210> SEQ ID NO 8
<211> LENGTH: 15
<212> TYPE: PRT
<213> ORGANISM: Measles virus

<400> SEQUENCE: 8

Leu Ser Glu Ile Lys Gly Val Ile Val His Arg Leu Glu Gly Val
1 5 10 15

<210> SEQ ID NO 9
<211> LENGTH: 20
<212> TYPE: PRT
<213> ORGANISM: Escherichia coli

<400> SEQUENCE: 9

Gly Ile Leu Glu Ser Arg Gly Ile Lys Ala Arg Ile Thr His Val Asp
1 5 10 15

Thr Glu Ser Tyr
20

<210> SEQ ID NO 10
<211> LENGTH: 17
<212> TYPE: PRT
<213> ORGANISM: Clostridium tetani

<400> SEQUENCE: 10

Trp Val Arg Asp Ile Ile Asp Asp Phe Thr Asn Glu Ser Ser Gln Lys
1 5 10 15

Thr

<210> SEQ ID NO 11
<211> LENGTH: 16
<212> TYPE: PRT
<213> ORGANISM: Clostridium tetani

<400> SEQUENCE: 11

Asp Val Ser Thr Ile Val Pro Tyr Ile Gly Pro Ala Leu Asn His Val
1 5 10 15

<210> SEQ ID NO 12
<211> LENGTH: 25
<212> TYPE: PRT
<213> ORGANISM: Chlamydia trachomatis

<400> SEQUENCE: 12

Ala Leu Asn Ile Trp Asp Arg Phe Asp Val Phe Cys Thr Leu Gly Ala
1 5 10 15

Thr Thr Gly Tyr Leu Lys Gly Asn Ser
20 25

<210> SEQ ID NO 13

-continued

<211> LENGTH: 23
<212> TYPE: PRT
<213> ORGANISM: Diphtheria

<400> SEQUENCE: 13

```
Asp Ser Glu Thr Ala Asp Asn Leu Glu Lys Thr Val Ala Ala Leu Ser
1               5                   10                  15

Ile Leu Pro Gly His Gly Cys
            20
```

<210> SEQ ID NO 14
<211> LENGTH: 39
<212> TYPE: PRT
<213> ORGANISM: Diphtheria

<400> SEQUENCE: 14

```
Glu Glu Ile Val Ala Gln Ser Ile Ala Leu Ser Ser Leu Met Val Ala
1               5                   10                  15

Gln Ala Ile Pro Leu Val Gly Glu Leu Val Asp Ile Gly Phe Ala Ala
            20                  25                  30

Thr Asn Phe Val Glu Ser Cys
        35
```

<210> SEQ ID NO 15
<211> LENGTH: 21
<212> TYPE: PRT
<213> ORGANISM: Plasmodium falciparum

<400> SEQUENCE: 15

```
Asp His Glu Lys Lys His Ala Lys Met Glu Lys Ala Ser Ser Val Phe
1               5                   10                  15

Asn Val Val Asn Ser
            20
```

<210> SEQ ID NO 16
<211> LENGTH: 17
<212> TYPE: PRT
<213> ORGANISM: Schistosoma mansoni

<400> SEQUENCE: 16

```
Lys Trp Phe Lys Thr Asn Ala Pro Asn Gly Val Asp Glu Lys His Arg
1               5                   10                  15

His
```

<210> SEQ ID NO 17
<211> LENGTH: 14
<212> TYPE: PRT
<213> ORGANISM: Escherichia coli

<400> SEQUENCE: 17

```
Gly Leu Gln Gly Lys His Ala Asp Ala Val Lys Ala Lys Gly
1               5                   10
```

<210> SEQ ID NO 18
<211> LENGTH: 19
<212> TYPE: PRT
<213> ORGANISM: Escherichia coli

<400> SEQUENCE: 18

```
Gly Leu Ala Ala Gly Leu Val Gly Met Ala Ala Asp Ala Met Val Glu
1               5                   10                  15

Asp Val Asn
```

-continued

<210> SEQ ID NO 19
<211> LENGTH: 20
<212> TYPE: PRT
<213> ORGANISM: Escherichia coli

<400> SEQUENCE: 19

```
Ser Thr Glu Thr Gly Asn Gln His His Tyr Gln Thr Arg Val Val Ser
1               5                   10                  15

Asn Ala Asn Lys
            20
```

<210> SEQ ID NO 20
<211> LENGTH: 20
<212> TYPE: PRT
<213> ORGANISM: Hepatitis B virus

<400> SEQUENCE: 20

```
Ser Asp Phe Phe Pro Ser Val Arg Asp Leu Leu Asp Thr Ala Ser Ala
1               5                   10                  15

Leu Tyr Arg Glu
            20
```

<210> SEQ ID NO 21
<211> LENGTH: 12
<212> TYPE: PRT
<213> ORGANISM: Chlamydia trachomatis

<400> SEQUENCE: 21

```
Thr Ile Asn Lys Pro Lys Gly Tyr Val Gly Lys Glu
1               5                   10
```

<210> SEQ ID NO 22
<211> LENGTH: 15
<212> TYPE: PRT
<213> ORGANISM: Measles virus

<400> SEQUENCE: 22

```
Leu Ser Glu Ile Lys Gly Val Ile Val His Arg Leu Glu Gly Val
1               5                   10                  15
```

<210> SEQ ID NO 23
<211> LENGTH: 16
<212> TYPE: PRT
<213> ORGANISM: Measles virus

<400> SEQUENCE: 23

```
Asp Leu Ser Asp Leu Lys Gly Leu Leu Leu His Lys Leu Asp Gly Leu
1               5                   10                  15
```

<210> SEQ ID NO 24
<211> LENGTH: 16
<212> TYPE: PRT
<213> ORGANISM: Measles virus

<400> SEQUENCE: 24

```
Glu Ile Ser Glu Ile Arg Gly Ile Ile Ile His Arg Ile Glu Gly Ile
1               5                   10                  15
```

<210> SEQ ID NO 25
<211> LENGTH: 16
<212> TYPE: PRT
<213> ORGANISM: Measles virus

<400> SEQUENCE: 25

Asp Val Ser Asp Val Lys Gly Val Val Val His Lys Val Asp Gly Val
1 5 10 15

<210> SEQ ID NO 26
<211> LENGTH: 16
<212> TYPE: PRT
<213> ORGANISM: Measles virus

<400> SEQUENCE: 26

Asp Phe Ser Asp Phe Lys Gly Phe Phe Phe His Lys Phe Asp Gly Phe
1 5 10 15

<210> SEQ ID NO 27
<211> LENGTH: 15
<212> TYPE: PRT
<213> ORGANISM: Measles virus

<400> SEQUENCE: 27

Ile Ser Glu Ile Lys Gly Val Ile Val His Lys Ile Glu Gly Ile
1 5 10 15

<210> SEQ ID NO 28
<211> LENGTH: 15
<212> TYPE: PRT
<213> ORGANISM: Measles virus

<400> SEQUENCE: 28

Met Thr Glu Ile Arg Thr Val Ile Val Thr Arg Met Glu Thr Met
1 5 10 15

<210> SEQ ID NO 29
<211> LENGTH: 15
<212> TYPE: PRT
<213> ORGANISM: Measles virus

<400> SEQUENCE: 29

Leu Ser Glu Ile Lys Gly Val Ile Val His Lys Leu Glu Gly Val
1 5 10 15

<210> SEQ ID NO 30
<211> LENGTH: 15
<212> TYPE: PRT
<213> ORGANISM: Measles virus

<400> SEQUENCE: 30

Ile Ser Glu Ile Lys Gly Val Ile Val His Lys Ile Glu Gly Ile
1 5 10 15

<210> SEQ ID NO 31
<211> LENGTH: 15
<212> TYPE: PRT
<213> ORGANISM: Measles virus

<400> SEQUENCE: 31

Ile Thr Glu Ile Arg Thr Val Ile Val Thr Arg Ile Glu Thr Ile
1 5 10 15

<210> SEQ ID NO 32
<211> LENGTH: 15
<212> TYPE: PRT
<213> ORGANISM: Measles virus

<400> SEQUENCE: 32

Met Ser Glu Ile Lys Gly Val Ile Val His Lys Leu Glu Gly Met
1 5 10 15

<210> SEQ ID NO 33
<211> LENGTH: 15
<212> TYPE: PRT
<213> ORGANISM: Measles virus

<400> SEQUENCE: 33

Leu Thr Glu Met Arg Thr Val Ile Val Thr Arg Met Glu Thr Val
1 5 10 15

<210> SEQ ID NO 34
<211> LENGTH: 15
<212> TYPE: PRT
<213> ORGANISM: Measles virus

<400> SEQUENCE: 34

Ile Ser Glu Ile Lys Gly Val Ile Val His Lys Ile Glu Gly Ile
1 5 10 15

<210> SEQ ID NO 35
<211> LENGTH: 15
<212> TYPE: PRT
<213> ORGANISM: Measles virus

<400> SEQUENCE: 35

Ile Thr Glu Ile Arg Thr Val Ile Val Thr Arg Ile Glu Thr Ile
1 5 10 15

<210> SEQ ID NO 36
<211> LENGTH: 15
<212> TYPE: PRT
<213> ORGANISM: Measles virus

<400> SEQUENCE: 36

Met Ser Glu Met Lys Gly Val Ile Val His Lys Met Glu Gly Met
1 5 10 15

<210> SEQ ID NO 37
<211> LENGTH: 15
<212> TYPE: PRT
<213> ORGANISM: Measles virus

<400> SEQUENCE: 37

Leu Thr Glu Ile Arg Thr Val Ile Val Thr Arg Leu Glu Thr Val
1 5 10 15

<210> SEQ ID NO 38
<211> LENGTH: 19
<212> TYPE: PRT
<213> ORGANISM: Measles virus

<400> SEQUENCE: 38

Ile Ser Ile Ser Glu Ile Lys Gly Val Ile Val His Lys Ile Glu Gly
1 5 10 15

Ile Leu Phe

<210> SEQ ID NO 39
<211> LENGTH: 19
<212> TYPE: PRT
<213> ORGANISM: Measles virus

<400> SEQUENCE: 39

Ile Ser Met Thr Glu Ile Arg Thr Val Ile Val Thr Arg Met Glu Thr
1 5 10 15

Met Leu Phe

<210> SEQ ID NO 40
<211> LENGTH: 19
<212> TYPE: PRT
<213> ORGANISM: Measles virus

<400> SEQUENCE: 40

Ile Ser Leu Ser Glu Ile Lys Gly Val Ile Val His Lys Leu Glu Gly
1 5 10 15

Val Leu Phe

<210> SEQ ID NO 41
<211> LENGTH: 19
<212> TYPE: PRT
<213> ORGANISM: Measles virus

<400> SEQUENCE: 41

Ile Ser Ile Ser Glu Ile Lys Gly Val Ile Val His Lys Ile Glu Gly
1 5 10 15

Ile Leu Phe

<210> SEQ ID NO 42
<211> LENGTH: 19
<212> TYPE: PRT
<213> ORGANISM: Measles virus

<400> SEQUENCE: 42

Ile Ser Ile Thr Glu Ile Arg Thr Val Ile Val Thr Arg Ile Glu Thr
1 5 10 15

Ile Leu Phe

<210> SEQ ID NO 43
<211> LENGTH: 19
<212> TYPE: PRT
<213> ORGANISM: Measles virus

<400> SEQUENCE: 43

Ile Ser Leu Ser Glu Ile Lys Gly Val Ile Val His Lys Leu Glu Gly
1 5 10 15

Met Leu Phe

<210> SEQ ID NO 44
<211> LENGTH: 19
<212> TYPE: PRT
<213> ORGANISM: Measles virus

<400> SEQUENCE: 44

Ile Ser Met Thr Glu Met Arg Thr Val Ile Val Thr Arg Met Glu Thr
1 5 10 15

Val Leu Phe

<210> SEQ ID NO 45
<211> LENGTH: 19
<212> TYPE: PRT
<213> ORGANISM: Measles virus

<400> SEQUENCE: 45

Ile Ser Leu Thr Glu Ile Arg Thr Val Ile Val Thr Arg Leu Glu Thr
1 5 10 15

Val Leu Phe

<210> SEQ ID NO 46
<211> LENGTH: 19
<212> TYPE: PRT
<213> ORGANISM: Measles virus

<400> SEQUENCE: 46

Ile Ser Ile Thr Glu Ile Arg Thr Val Ile Val Thr Arg Ile Glu Thr
1 5 10 15

Ile Leu Phe

<210> SEQ ID NO 47
<211> LENGTH: 19
<212> TYPE: PRT
<213> ORGANISM: Measles virus

<400> SEQUENCE: 47

Ile Ser Ile Ser Glu Ile Lys Gly Val Ile Val His Lys Ile Glu Gly
1 5 10 15

Ile Leu Phe

<210> SEQ ID NO 48
<211> LENGTH: 19
<212> TYPE: PRT
<213> ORGANISM: Measles virus

<400> SEQUENCE: 48

Ile Ser Ile Thr Glu Ile Arg Thr Val Ile Val Thr Arg Ile Glu Thr
1 5 10 15

Ile Leu Phe

<210> SEQ ID NO 49
<211> LENGTH: 19
<212> TYPE: PRT
<213> ORGANISM: Measles virus

<400> SEQUENCE: 49

Ile Ser Met Ser Glu Met Lys Gly Val Ile Val His Lys Met Glu Gly
1 5 10 15

Met Leu Phe

<210> SEQ ID NO 50
<211> LENGTH: 19
<212> TYPE: PRT
<213> ORGANISM: Measles virus

<400> SEQUENCE: 50

Ile Ser Leu Thr Glu Ile Arg Thr Val Ile Val Thr Arg Leu Glu Thr
1 5 10 15

Val Leu Phe

<210> SEQ ID NO 51
<211> LENGTH: 19
<212> TYPE: PRT
<213> ORGANISM: Measles virus

<400> SEQUENCE: 51

Ile Ser Ile Thr Glu Ile Lys Gly Val Ile Val His Arg Ile Glu Thr
1 5 10 15

Ile Leu Phe

<210> SEQ ID NO 52
<211> LENGTH: 15

<212> TYPE: PRT
<213> ORGANISM: Hepatitis B virus

<400> SEQUENCE: 52

Phe Phe Leu Leu Thr Arg Ile Leu Thr Ile Pro Gln Ser Leu Asp
1 5 10 15

<210> SEQ ID NO 53
<211> LENGTH: 18
<212> TYPE: PRT
<213> ORGANISM: Hepatitis B virus

<400> SEQUENCE: 53

Lys Lys Lys Phe Phe Leu Leu Thr Arg Ile Leu Thr Ile Pro Gln Ser
1 5 10 15

Leu Asp

<210> SEQ ID NO 54
<211> LENGTH: 14
<212> TYPE: PRT
<213> ORGANISM: Hepatitis B virus

<400> SEQUENCE: 54

Phe Phe Leu Leu Thr Arg Ile Leu Thr Ile Pro Gln Ser Leu
1 5 10

<210> SEQ ID NO 55
<211> LENGTH: 18
<212> TYPE: PRT
<213> ORGANISM: Hepatitis B virus

<400> SEQUENCE: 55

Lys Lys Lys Leu Phe Leu Leu Thr Lys Leu Leu Thr Leu Pro Gln Ser
1 5 10 15

Leu Asp

<210> SEQ ID NO 56
<211> LENGTH: 18
<212> TYPE: PRT
<213> ORGANISM: Hepatitis B virus

<400> SEQUENCE: 56

Arg Arg Arg Ile Lys Ile Ile Thr Arg Ile Ile Thr Ile Pro Leu Ser
1 5 10 15

Ile Arg

<210> SEQ ID NO 57
<211> LENGTH: 18
<212> TYPE: PRT
<213> ORGANISM: Hepatitis B virus

<400> SEQUENCE: 57

Lys Lys Lys Val Arg Val Val Thr Lys Val Val Thr Val Pro Ile Ser
1 5 10 15

Val Asp

<210> SEQ ID NO 58
<211> LENGTH: 18
<212> TYPE: PRT
<213> ORGANISM: Hepatitis B virus

<400> SEQUENCE: 58

Lys Lys Lys Phe Phe Phe Phe Thr Lys Phe Phe Thr Phe Pro Val Ser

-continued 1 5 10 15

Phe Asp

<210> SEQ ID NO 59
<211> LENGTH: 18
<212> TYPE: PRT
<213> ORGANISM: Hepatitis B virus

<400> SEQUENCE: 59

Lys Lys Lys Leu Phe Leu Leu Thr Lys Leu Leu Thr Leu Pro Phe Ser
1 5 10 15

Leu Asp

<210> SEQ ID NO 60
<211> LENGTH: 18
<212> TYPE: PRT
<213> ORGANISM: Hepatitis B virus

<400> SEQUENCE: 60

Lys Lys Lys Ile Ile Thr Ile Thr Arg Ile Ile Thr Ile Ile Thr Thr
1 5 10 15

Ile Asp

<210> SEQ ID NO 61
<211> LENGTH: 17
<212> TYPE: PRT
<213> ORGANISM: Hepatitis B virus

<400> SEQUENCE: 61

Lys Lys Lys Ile Ile Thr Ile Thr Arg Ile Ile Thr Ile Ile Thr Thr
1 5 10 15

Ile

<210> SEQ ID NO 62
<211> LENGTH: 18
<212> TYPE: PRT
<213> ORGANISM: Hepatitis B virus

<400> SEQUENCE: 62

Lys Lys Lys Met Met Thr Met Thr Arg Met Ile Thr Met Ile Thr Thr
1 5 10 15

Ile Asp

<210> SEQ ID NO 63
<211> LENGTH: 16
<212> TYPE: PRT
<213> ORGANISM: Hepatitis B virus

<400> SEQUENCE: 63

Phe Ile Thr Met Asp Thr Lys Phe Leu Leu Ala Ser Thr His Ile Leu
1 5 10 15

<210> SEQ ID NO 64
<211> LENGTH: 19
<212> TYPE: PRT
<213> ORGANISM: Hepatitis B virus

<400> SEQUENCE: 64

Lys Lys Lys Phe Ile Thr Met Asp Thr Lys Phe Leu Leu Ala Ser Thr
1 5 10 15

His Ile Leu

<210> SEQ ID NO 65
<211> LENGTH: 42
<212> TYPE: PRT
<213> ORGANISM: Homo sapiens

<400> SEQUENCE: 65

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly Gly Val Val Ile Ala
35 40

<210> SEQ ID NO 66
<211> LENGTH: 28
<212> TYPE: PRT
<213> ORGANISM: Homo sapiens

<400> SEQUENCE: 66

Asp Ala Glu Phe Arg His Asp Ser Gly Tyr Glu Val His His Gln Lys
1 5 10 15

Leu Val Phe Phe Ala Glu Asp Val Gly Ser Asn Lys
20 25

<210> SEQ ID NO 67
<211> LENGTH: 14
<212> TYPE: PRT
<213> ORGANISM: Homo sapiens

<400> SEQUENCE: 67

Asp Ala Glu Phe Arg His Asp Ser Gly Tyr Glu Val His His
1 5 10

<210> SEQ ID NO 68
<211> LENGTH: 12
<212> TYPE: PRT
<213> ORGANISM: Homo sapiens

<400> SEQUENCE: 68

Asp Ala Glu Phe Arg His Asp Ser Gly Tyr Glu Val
1 5 10

<210> SEQ ID NO 69
<211> LENGTH: 10
<212> TYPE: PRT
<213> ORGANISM: Homo sapiens

<400> SEQUENCE: 69

Asp Ala Glu Phe Arg His Asp Ser Gly Tyr
1 5 10

<210> SEQ ID NO 70
<211> LENGTH: 45
<212> TYPE: PRT
<213> ORGANISM: Hepatitis B virus

<400> SEQUENCE: 70

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Gly Phe Phe
20 25 30

Leu Leu Thr Arg Ile Leu Thr Ile Pro Gln Ser Leu Asp
35 40 45

<210> SEQ ID NO 71
<211> LENGTH: 30
<212> TYPE: PRT
<213> ORGANISM: Measles virus

<400> SEQUENCE: 71

```
Asp Ala Glu Phe Arg His Asp Ser Gly Tyr Lys Ile Ser Ile Thr Glu
1               5                   10                  15

Ile Lys Gly Val Ile Val His Arg Ile Glu Thr Ile Leu Phe
            20                  25                  30
```

<210> SEQ ID NO 72
<211> LENGTH: 32
<212> TYPE: PRT
<213> ORGANISM: Measles virus

<400> SEQUENCE: 72

```
Asp Ala Glu Phe Arg His Asp Ser Gly Tyr Glu Val Lys Ile Ser Ile
1               5                   10                  15

Thr Glu Ile Lys Gly Val Ile Val His Arg Ile Glu Thr Ile Leu Phe
            20                  25                  30
```

<210> SEQ ID NO 73
<211> LENGTH: 34
<212> TYPE: PRT
<213> ORGANISM: Measles virus

<400> SEQUENCE: 73

```
Asp Ala Glu Phe Arg His Asp Ser Gly Tyr Glu Val His His Lys Ile
1               5                   10                  15

Ser Ile Thr Glu Ile Lys Gly Val Ile Val His Arg Ile Glu Thr Ile
            20                  25                  30

Leu Phe
```

<210> SEQ ID NO 74
<211> LENGTH: 48
<212> TYPE: PRT
<213> ORGANISM: Measles virus

<400> SEQUENCE: 74

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Lys Ile Ser Ile
            20                  25                  30

Thr Glu Ile Lys Gly Val Ile Val His Arg Ile Glu Thr Ile Leu Phe
        35                  40                  45
```

<210> SEQ ID NO 75
<211> LENGTH: 34
<212> TYPE: PRT
<213> ORGANISM: Measles virus

<400> SEQUENCE: 75

```
Asp Ala Glu Phe Arg His Asp Ser Gly Tyr Glu Val His His Lys Ile
1               5                   10                  15

Ser Ile Ser Glu Ile Lys Gly Val Ile Val His Lys Ile Glu Gly Ile
            20                  25                  30

Leu Phe
```

<210> SEQ ID NO 76

-continued

```
<211> LENGTH: 34
<212> TYPE: PRT
<213> ORGANISM: Measles virus

<400> SEQUENCE: 76

Asp Ala Glu Phe Arg His Asp Ser Gly Tyr Glu Val His His Lys Ile
1               5                   10                  15

Ser Ile Thr Glu Ile Arg Thr Val Ile Val Thr Arg Ile Glu Thr Ile
            20                  25                  30

Leu Phe


<210> SEQ ID NO 77
<211> LENGTH: 6
<212> TYPE: PRT
<213> ORGANISM: Artificial
<220> FEATURE:
<223> OTHER INFORMATION: synthetic peptide linker
<220> FEATURE:
<221> NAME/KEY: MISC_FEATURE
<222> LOCATION: (3)..(3)
<223> OTHER INFORMATION: X = ANY AMINO ACID
<220> FEATURE:
<221> NAME/KEY: MISC_FEATURE
<222> LOCATION: (5)..(5)
<223> OTHER INFORMATION: X = ANY AMINO ACID

<400> SEQUENCE: 77

Pro Pro Xaa Pro Xaa Pro
1               5
```

IMMUNOGENIC PEPTIDE COMPOSITION FOR THE PREVENTION AND TREATMENT OF ALZHEIMER'S DISEASE

CROSS REFERENCE TO RELATED APPLICATION

This application is a divisional application, which claims the benefit of U.S. patent application Ser. No. 10/861,614 entitled "Immunogenic Peptide Composition Comprising A Promiscuous Helper T Cell Epitope And An N-Terminal Fragment Of ABeta$_{1-42}$ Peptide", filed Jun. 4, 2004, which is a divisional application of, and claims the benefit to, U.S. patent application Ser. No. 09/865,294 entitled "Immunogenic Peptide Composition Comprising Measles Virus F Protein T Helper Cell Epitope (MVF Th1-16) And N-Terminus Of B-Amyloid Peptide", filed on May 25, 2001, (now U.S. Pat. No. 6,906,169), all of which are herein incorporated by reference.

FIELD OF THE INVENTION

The present invention relates to a composition comprising a peptide immunogen useful for the prevention and treatment of Alzheimer's Disease. More particularly, the peptide immunogen comprises a main functional/regulatory site, an N-terminal fragment of Amyloid β (Aβ) peptide linked to a helper T cell epitope (Th) having multiple class II MHC binding motifs. The peptide immunogen elicits a site-directed immune response against the main functional/regulatory site of the Aβ peptide and generate antibodies, which are highly cross-reactive to the soluble Aβ$_{1-42}$ peptide and the amyloid plaques formed in the brain of Alzheimer's Disease patients. The antibodies elicited being cross reactive to the soluble Aβ$_{1-42}$ peptide, promote fibril disaggregation and inhibit fibrillar aggregation leading to immunoneutralization of the "soluble Aβ-derived toxins"; and being cross-reactive to the amyloid plaques, accelerate the clearance of these plaques from the brain. Thus, the composition of the invention comprising the peptide immunogen is useful for the prevention and treatment of Alzheimer's Disease.

BACKGROUND OF THE INVENTION

Alzheimer's Disease (AD) is a chronic, neurodegenerative disorder characterized by a loss of cognitive ability and severe behavioral abnormalities in a patient leading to the eventual death of the patient. There are currently 2.5 to 4.0 million AD patients in the U.S. and 17 to 25 million worldwide. It is the fourth leading cause of death in Western cultures, preceded only by heart disease, cancer, and stroke. ARICEPT®, an acetylcholinesterase inhibitor has been approved by the FDA for decelerating the rate of decline of Alzheimer patients. However, it is effective only for a limited period of time and in some patients. Up to the present there is no definitive treatment or cure for this devastating disease.

Two microscopic deposits, i.e., neurofibrillary tangles (NFT) and senile amyloid plaques, were identified by Alois Alzheimer as the pathologic hallmarks of the disease. The neurofibrillary tangles consist of two 10 nm wide filaments twisted around each other, referred to as paired helical filaments (PHFs), a major component of which is phosphorylated tau. The phosphorylation of serine at amino acid 262 of the tau protein represents a crucial step leading to physiological dysfunction of tau. PHFs are intracellular and are found in many of the abnormal dendritic and axonal processes, or neurites that make up the periphery of senile amyloid plaques.

The senile amyloid plaques consist of disorganized neurophil filaments in an area of up to 150 μm in cross section with an extra-cellular core of amyloid deposit. The cerebral amyloid plaques are ultrastructurally distinct from PHFs and consist of 4-8 nm wide filaments that are not wound together in pairs. The plaque core consists of aggregates of a peptide, initially referred to as A4, with a relative molecular mass (M) of about 4,000 (Masters et al., Proc Natl Acad Sci USA, 1985, 82:4245-4249).

A partial amino acid sequence of A4, now renamed amyloid β peptide (or Aβ$_{1-42}$), shows that it is similar to the amyloid β protein isolated from cerebral blood vessels of patients with Alzheimer's disease or Down's syndrome (Glenner and Wong, Biochem Biophys Res Comm, 1984; 120:885-890; 122:1131-1135).

Aβ$_{1-42}$ has been hypothesized to be related to AD for a number of reasons. Firstly, in peripheral amyloidoses, e.g., primary light chain disease or secondary AA amyloidosis, large amyloid burdens strongly correlate with tissue and organ dysfunction. Secondly, amyloid plaque density positively correlates with premortem dementia scores in AD. Thirdly, Aβ$_{1-42}$ deposition is the earliest neuropathological marker in AD and related disorders such as Down's syndrome, where it can precede NFT formation by 2-3 decades. Fourthly, β-amyloidosis is relatively specific to AD and related disorders. Fifthly, Aβ$_{1-42}$ is toxic to neurons (Yankner et al., Science, 1990; 250:279-282). Lastly, missense mutations in the structural amyloid precursor protein (APP) gene cause early onset of familial AD (Goate et al., Nature, 1991; 349:704-706; Mullan et al., Nature Genetics, 1992; 1:345-347). Notably, one such mutation causes dramatic Aβ$_{1-42}$ overproduction (Citron et al., Nature, 1992; 360:672-674).

In 1987, Kang et al. (Nature, 1987; 325:733-737) and three other groups (see 1987 status reports by Anderton, Nature, 1987; 325:658-659 and Barnes, Science, 1987; 235:846-847) independently cloned the gene from which Aβ$_{1-42}$ is derived. This gene, now known as the amyloid precursor protein (APP), encodes a protein of 695 amino-acid residues with a MW of about 79,000 that is expressed in virtually all tissues. There are at least five splicing variants of APP, four of which contain the β-amyloid peptide sequence.

Four genes have been implicated in familial forms of AD. Three of the genes, βAPP, presenilin I, and presenilin 2, when mutated, cause autosomal dominant early forms of AD. The fourth gene, Apolipoprotein E, has a naturally occurring polymorphic form, ApoE4, that represents a major genetic risk factor for the development of the disease. The concept that alterations in several distinct genes can lead to a chronic imbalance between Aβ$_{1-42}$ production and its clearance, with the resulting aggregation of first the 42-residue and then the 40-residue peptide into cytotoxic plaques, is supported by available evidence. The evidence strongly suggests that defects in each of these four genes predispose the AD phenotype by (1) enhancing the production and/or the deposition of Aβ$_{1-42}$ peptides or (2) by decreasing the clearance of ApoE4 from tissue (Selkoe, J Biol Chem, 1996; 271:18295-18298).

From available data, it appears that aggregated but not monomeric Aβ$_{1-42}$ peptides can induce cell dysfunction and death in vitro by a range of presumably interrelated mechanisms. These include oxidative injury (Thomas et al., Nature, 1996; 380:168-171; Behl et al., Cell, 1994; 77:817-827), alterations in intracellular calcium homeostasis (Arispe et al., Proc Natl Acad Sci USA, 1993; 90:567-571), and cytoskeletal reorganization (Busciglio et al., Neuron, 1995; 14:879-888). Sufficient knowledge of some of the principal steps in the amyloid-induced cascade has emerged, even though the cascade hypothesis is hotly contested.

Pharmalogical approaches of identifying small molecules which could inhibit one or another step of the amyloid induced cascade are now well under way. Of particular interest are two approaches: attempts to interfere with the aggregation of $A\beta_{1-42}$ peptides by decreasing the secretion of $A\beta_{1-42}$ peptides from neuronal and glial cells or inhibit the toxicity that these extracellular aggregates produce on neurons and glial cells and their processes. A third approach which attempts to control the specialized inflammatory response that appears to be triggered by aggregated $A\beta_{1-42}$ (including microglial stimulation, activation of the classical complement cascade, cytokine release, and reactive astrocytosis) may prove to be of benefit to Alzheimer's patients.

Aside from the above-mentioned pharmacological approaches for AD intervention, immunological interventions have also been attempted. Soloman et al. (Proc Natl Acad. Sci, 1996; 93:452-455; Proc Natl Aca. Sci, 1997; 94:4109-4112) showed that three specific monoclonal antibodies, directed toward a site in the N-terminal region of the human $A\beta_{1-42}$ peptide, bind in varying degrees to preformed fibrils leading to their disaggregation and inhibition of their neurotoxic effect. The antibodies were also found to prevent the formation of fibrillar $A\beta_{1-42}$. Solomon et al. (WO 01/18169) also attempted to prepare a phage display of an epitope of the $A\beta_{1-42}$ peptide and administering the phage displayed epitope or peptide containing the epitope intraperitonially to mice to elicit antibodies to the $A\beta_{1-42}$ peptide. In vitro testing with rat phenochromocytoma showed that a 1:5 dilution of the antisera prevented the neurotoxicity of $A\beta_{1-42}$. The antiserum at a dilution of 1:5 and 1:20 was also shown to disrupt the fibril structure of Aβ in vitro with extensive deterioration of fibril morphology. However, the adjuvant used was for the first injection was Complete Freund's Adjuvant with the incomplete Freund's Adjuvant for the second injection. The adjuvants used are entirely unsuitable for use in humans. Moreover, the levels of antibodies generated were too low to be effective despite the use of these harsh adjuvants.

Subsequently, Schenk et al. (Nature, 1999; 400:173-177) showed that immunization with $A\beta_{1-42}$ peptide inhibits the formation of amyloid plaques and the associated dystrophic neurites in a mouse model of AD. However, due to the low immunogenicity of the $A\beta_{1-42}$ peptide, the method employed required repeated administrations of the antigen with a harsh lesion-forming adjuvant to obtain the higher levels of anti-$A\beta_{1-42}$ plaque antibodies necessary to affect plaque formation. Moreover, it was cautioned that immunization with $A\beta_{1-42}$ might induce more accumulation of the toxic amyloid itself (Araujo, D M & Cotman, C W, Brain Res, 1992; 569, 141-145).

Despite these criticisms, additional studies in transgenic AD mouse models through similar active immunization have lent credence to the immunoprophylaxis and immunotherapeutic approaches for AD. Janus et al. (Nature, 2000; 408: 979-982) described $A\beta_{1-42}$ peptide immunization in a mouse model for AD that reduced behavior impairment and plaques. Morgan et al. (Nature, 2000; 408:982-985) described $A\beta_{1-42}$ peptide vaccination to prevent memory loss in the mouse model.

Direct support for the effectiveness of immune therapy came from the observation that peripheral administration of antibodies, monoclonal or polyclonal, against Aβ-peptide reduced amyloid burden (WO 99/27944; Bard et al., Nature Medicine, 2000; 6:916-919). Despite relatively modest serum levels, these passively administered antibodies, monoclonal 3D6 (anti-$A\beta_{1-5}$) and 10D5 (anti-$A\beta_{1-12}$) or polyclonal anti-$A\beta_{1-42}$, were able to enter the central nervous system. There, the antibodies bound to plaques and induced clearance of pre-existing amyloid plaques. Bard et al., reported that when examined in an ex vivo assay with brain sections of PDAPP mice (i.e., mice transgenic for an APP mini-gene driven by a platelet-derived growth factor promoter) or AD patient brain tissue, antibodies against Aβ-peptide triggered microglial cells to clear plaques through Fc receptor-mediated phagocytosis and subsequent peptide degradation. This study demonstrated that passively administered antibodies against $A\beta_{1-42}$ peptide and the $A\beta_{1-42}$ N-terminus region reduced the extent of plaque deposition in a mouse model of AD; and that monoclonal antibodies or polyclonal antibodies elicited by site-directed vaccines are able to enter the CNS at therapeutically relevant levels.

Despite the promising findings of immunological intervention in mice model for AD, a vaccine against AD suitable for humans remains a long way off (Chapman, Nature, 2000; 408:915-916). The principal hurdles reside in the extensive work necessary to design and formulate an immunogenic composition that is useful in humans before a practicable vaccine for AD can be achieved. Some of the issues that rely on experimental data for guidance are: (1) What is the specific target site for antibody recognition within the Aβ? (2) In what form should the immunogen be presented? (3) What other sites need to be included before an immunogen is achieved that will elicit a therapeutic level of antibody? (4) What is an effective vaccine delivery system employing a clinically acceptable adjuvant for humans?

A major gap exists between what has been disclosed in the literature and what remains to be done. What is the suitable specific target site (i.e., the polymerized $A\beta_{1-42}$ plaque or the monomeric soluble $A\beta_{1-42}$ peptide) and how the specific site is to be engineered for immunological intervention. In spite of some 5,000 publications on $A\beta_{1-42}$ over the past decade, the amyloid cascade hypothesis is hotly debated and the issue: the form in which $A\beta_{1-42}$ should be used for intervention remains contentious. At the heart of the problem, argued by Terry and colleagues, is the weak correlation between fibrillar amyloid load and measures of neurological dysfunction (The Neuropathology of Alzheimer Disease and the Structure Basis of its Alterations, Ed. by Terry et al., Alzheimer Disease, p 187-206, Lippincott Williams and Wilkins, 1999).

In AD patients, amyloid deposits often form at a distance from the site of neuron damage. The best correlation with pathological dementia is loss of synaptic terminals. However, the loss of synaptic terminals correlates poorly with amyloid load. If the manifestations of disease correlate weakly with amyloid load, then what is the role of Aβ? The article by Klein et al, titled "Targeting small $A\beta_{1-42}$ oligomers: the solution to an Alzheimer's disease conumdrum?" (Trends in Neurosciences, 2001; 24:219-224) suggests that fibrils are not the only toxic form of Aβ, and perhaps not the neurotoxin that is most relevant to AD. Small oligomers and protofibrils, also termed as $A\beta_{1-42}$ derived diffusible ligands (ADDLs), may also have potent toxic neurological activity.

An AD vaccine for successful immunological intervention will require an immunogen designed to elicit site-directed high affinity antibodies that bind to the senile plaques in the brain tissue to accelerate the clearance of the plaque by the Glial cells, and immunoneutralize the soluble Aβ-derived toxins.

The problem of raising high affinity site-directed antibodies against poorly immunogenic site-specific peptides have been known for decades. Immunologists and vaccinologists often resort to the classical hapten [peptide]-carrier protein conjugate approach as demonstrated in WO 99/27944. For the development of a site-directed vaccine against AD, Frenkel et al. attempted immunization against $A\beta_{1-42}$ plaques through "EFRH"-phage administration (Proc Natl Acad. Sci 2000; 97:11455-11459, WO 01/18169) as mentioned above.

The approaches: using $A\beta_{1-42}$ peptide aggregate or $A\beta_{1-42}$ peptide fragment-carrier protein conjugates (WO99/27944) and using filamentous phage displaying "EFRH peptide" as the agents to induce immune responses against an amyloid deposit in a patient, are cumbersome and ineffective. For example, after the fourth immunization of 1011 phages displaying the EFRH epitope, >95% of the antibodies in the guinea pig immune sera are against the phages. Only a small population (<5%) of the antibodies is against the soluble $A\beta_{1-42}$ peptide (Frenkel et al., Vaccine 2001, 19:2615-2619, WO 01/18169).

Less cumbersome methods were described in EP 526,511 and WO 99/27944, which disclosed the administration of $A\beta_{1-42}$ peptide to treat patients with pre-established AD and the administration of $A\beta_{1-42}$ or other immunogens to a patient under conditions that generate a "beneficial" immune response in the AD patient. However, a review of WO99/27944 show that there are major deficiencies in the vaccine design disclosed therein.

In particular, the problem lies in the lack of a pharmaceutically acceptable and effective vaccine delivery system. WO99/27944 disclosed $A\beta_{1-42}$ or active fragments of $A\beta_{1-42}$ conjugated to a carrier molecule such as cholera toxin as the active vaccine component. See page 4 of WO 99/27944. Although page 5 taught that a pharmaceutical composition comprising the immunogen should be free of Complete Freund's Adjuvant [CFA], the only examples showing the efficacy of the $A\beta_{1-42}$ vaccine for the treatment of AD in transgenic mice employed large doses of aggregated $A\beta_{42}$ peptide in CFA. Despite repetitive recital of preferred adjuvants that are to be used with the disclosed immunogenic agents to enhance the immune response, experimental data showed that only the formulations employing CFA/ICFA provided a sufficiently high titer of antibodies. See, page 25 of WO 99/27944. In example 1, the prophylactic efficacy of $A\beta_{1-42}$ against AD was demonstrated in PDAPP mice. However, the formulations administered consist a dose of 100 μg per mouse of aggregated Aβ42 emulsified in Complete Freund's Adjuvant [CFA] (p 34 of WO 99/27944) followed by multiple booster doses of the same $A\beta_{1-42}$ peptide emulsified in Incomplete Freund's Adjuvant. In Example IX, the immune responses in mice to different adjuvants were studied. When the adjuvants: MPL, Alum, QS21, and CFA/ICFA were used with the purportedly potent immunogen AN1792 (i.e., aggregated human $A\beta_{42}$), the level of antibodies to $A\beta_{1-4}$ were reduced at a statistically significant level in comparison to mice that received the CFA/ICFA vaccines. See, Table 9, and pages 59-64 of WO 99/27944.

In the case where $A\beta_{1-42}$ peptide fragments were used (human $A\beta_{1-42}$ peptides of amino acids 1-5, 1-12, 13-28, and 33-42), each fragment was conjugated to sheep anti-mouse IgG as the protein carrier. In a later disclosure, the efficacy of antibodies to Aβ peptide fragments could only be shown by passive immunization with monoclonal antibodies (Bard et al., Nature Medicine 2000; 6:916-919). The efficacy of these fragments conjugated to sheep anti-mouse IgG was not shown. Therefore, the only immunogen shown to be effective was the aggregated $A\beta_{1-42}$ peptide in CFA/ICFA.

Up to the present, all of the vaccine formulations shown to be effective employed CFA/IFA as the adjuvant. Peptide immunogens targeting $A\beta_{1-42}$ have thus far been prepared by conjugation of the various $A\beta_{1-42}$ fragments to sheep anti-mouse immunoglobulin, conjugation of synthetic $A\beta_{13-28}$ via m-maleimidobenzoyl-N-hydroxysuccinimide ester to anti-CD3 antibody, or aggregated $A\beta_{1-42}$ peptide alone. These immunogens, i.e., $A\beta_{42}$ peptide alone or $A\beta_{1-42}$ peptide-carrier protein conjugates, were emulsified with complete Freund's adjuvant for the first immunization, followed by subsequent boosts in incomplete Freund's adjuvant (Johnson-Wood et al., Proc Natl Acad Sci USA, 1997; 94:1550-1555; Seubert et al., Nature, 1992; 359:325-327; Schenk et al., Nature, 1999; 400: 173-177; Janus et al., Nature 2000; 408: 979-982; and Morgan et al., Nature, 2000; 408:982-985). The formulations disclosed in WO 99/27944 or others using CFA and ICFA as adjuvants cause lesions and are too harsh for use in humans. Thus, none of the vaccine compositions for AD described in the prior art are suitable for use in humans.

In summary, despite statements suggesting the potential of $A\beta_{1-42}$ peptide for the treatment of AD in view of the previous disclosures of Kline (EP 526,511), no problem solving vaccine formulations were really offered in WO99/27944 to address this key problem.

Another disadvantage with the peptide-carrier protein conjugates and $A\beta_{1-42}$ aggregates is that these molecules are highly complex and are difficult to characterize and it is difficult to develop effective quality control procedures for the manufacturing process. A further disadvantage is that, $A\beta_{1-42}$ peptide or its fragments are self molecules when administered to humans. Therefore, they are less immunogenic or non-immunogenic in humans. It is, thus, necessary to develop clinically acceptable vaccine formulations for administration in humans.

It is known that promiscuous Th epitopes may be employed to evoke efficient T cell help and may be combined with poorly immunogenic B cell epitopes to provide potent immunogens. Well-designed promiscuous Th/B cell epitope chimeric peptides have been shown to be useful in eliciting Th responses and resultant antibody responses in most members of a genetically diverse population expressing diverse MHC haplotypes. Promiscuous Th from a number of pathogens, such as measles virus F protein and hepatitis B virus surface antigen, are known. Tables 1 and 2 lists many of the known promiscuous Th that have been shown to be effective in potentiating a short poorly immunogenic peptide, the decapeptide hormone LHRH (U.S. Pat. Nos. 5,759,551, and 6,025,468).

Potent Th epitopes range in size from approximately 15-40 amino acid residues in length, often share common structural features, and may contain specific landmark sequences. For example, a common feature of a Th is that it contains amphipathic helices, alpha-helical structures with hydrophobic amino acid residues dominating one face of the helix and with charged and polar residues dominating the surrounding faces (Cease et al., Proc Natl Acad Sci USA, 1987; 84: 4249-4253). Th epitopes frequently contain additional primary amino acid patterns such as a Gly or charged residue followed by two to three hydrophobic residues, followed in turn by a charged or polar residue. This pattern defines what are called Rothbard sequences. Th epitopes often obey the 1, 4, 5, 8 rule, where a positively charged residue is followed by hydrophobic residues at the fourth, fifth and eighth positions after the charged residue. Since all of these structures are composed of common hydrophobic, charged and polar amino acids, each structure can exist simultaneously within a single Th epitope (Partidos et al., J Gen Virol, 1991; 72:1293). Most, if not all, of the promiscuous T cell epitopes fit at least one of the periodicities described above. These features may be incorporated into the designs of idealized artificial Th sites, including combinatorial Th epitopes. With respect to the design of combinatorial Th sites, lists of variable positions and preferred amino acids are available for MHC-binding motifs (Meister et al., Vaccine, 1995; 13:581-591). Furthermore, a method for producing combinatorial Th has been disclosed for combinatorial library peptides termed structured synthetic antigen library (Wang et al., WO 95/11998). Thus, the 1, 4, 5, 8 rule can be applied together with known combinatorial MHC-binding motifs to assign invariant and degenerate positions in a combinatorial Th site, and to select residues for the degenerate sites to vastly enlarge the range of immune responsiveness of an artificial Th. See, Table 2, WO 99/66957, and WO 95/11998.

Wang et al. (U.S. Pat. No. 5,759,551) suggested the use of immunostimulatory elements to render the self protein Amylin immunogenic. Wang et al. suggested the administration of immunogenic synthetic amylin peptides as vaccines for the treatment of non-insulin dependent diabetes mellitus (NIDDM), an amyloidogenic disease caused by overproduction of Amylin (column 19, lines 9-39, U.S. Pat. No. 5,759,551). Amylin is a 37 amino acid residue peptide hormone produced by the β cells in the islets of Langerhans. Overproduction of Amylin will result in the deposition of insoluble amyloid leading to amyloidogenic disease in the pancreas. Similar to the overproduction of Amylin, overproduction of the $Aβ_{1-42}$ peptide will lead to the deposition of insoluble amyloid in the brain of AD patients. However, there is limited sequence homology between Amylin and the $Aβ_{1-42}$ peptide. Only a short stretch of amino acids residues, VGSN, of Amylin32-35 corresponds to $Aβ_{24-27}$. Antibodies produced against the Amylin peptide are not expected to be cross reactive to soluble $Aβ_{1-42}$ peptides nor accelerate the clearance of amyloid plaques in the brain in view of the studies by Soloman et al. and Schenk et al., which showed that the sequence EFRH is critical.

It is the object of the invention to develop an immunogen that will enable the generation of high levels of high affinity antibodies against the N-terminal functional site of the $Aβ_{1-42}$ peptide with high cross-reactivity to the senile plaques in the brain of AD patients. The antibodies generated by binding to the $Aβ_{1-42}$ peptide and the senile plaques is expected to accelerate the clearance of these plaques from the brain, promote fibril disaggregation, inhibit fibrillar aggregation, and cause immunoneutralization of the "soluble Aβ-derived toxins" (also termed as Aβ-derived diffusible ligands or ADDLs).

It is a further objective of the present invention to develop a vaccine delivery vehicle that is suitable for human or veterinary use for the prophylaxis and treatment of Alzheimer's Disease.

BRIEF DESCRIPTION OF THE DRAWINGS

FIGS. 1*a*, and 1*d* show significant binding of antibodies to both senile plaques and Aβ plaques (both labelled as "P") on thioflavine S positive blood vessels (labelled as "BV"). The antibodies were generated in guinea pigs using $Aβ_{1-28}$-εK-MVF Th1-16 (SEQ ID NO:74) prepared in ISA51 water-in-oil emulsion. FIGS. 1*b* and 1*e* show the cross reactivity of antibodies raised against the same peptide immunogen in CFA/ICFA. FIGS. 1*c* and 1*f* show brain sections using preimmune sera.

FIGS. 2*a*, 2*b*, 2*c*, 2*d*, and 2*e* are photographs showing Immunoperoxidase staining of serial sections of AD brain with immune and preimmune sera at 1:100 dilution and under 40× magnification. FIGS. 2*a* and 2*d* showed that the antibodies in guinea pigs immunized with $Aβ_{1-28}$-εK-MVF Th1-16 (SEQ ID NO:74) prepared in ISA51 water-in-oil emulsion strongly stained the plaques (P) forming a pattern of cores. FIG. 2*b* is a photograph of the staining pattern of AD brain sections using the same immunogen in CFA/ICFA formulation. The anti-sera reacted predominantly with plaques on the blood vessels (BV). FIG. 2*c* is a photograph of an AD brain section with preimmune serum and showed no staining. FIG. 2*e* shows the brain section with hyperimmune sera generated by immunization with $Aβ_{1-28}$ peptide alone in CFA/ICFA showing a surprisingly weak staining pattern despite the strong reactivity with $Aβ_{1-28}$ by ELISA.

BRIEF DESCRIPTION OF THE INVENTION

Figures 1, 1A, 1B, 1C, 1D, 1E, 1F:
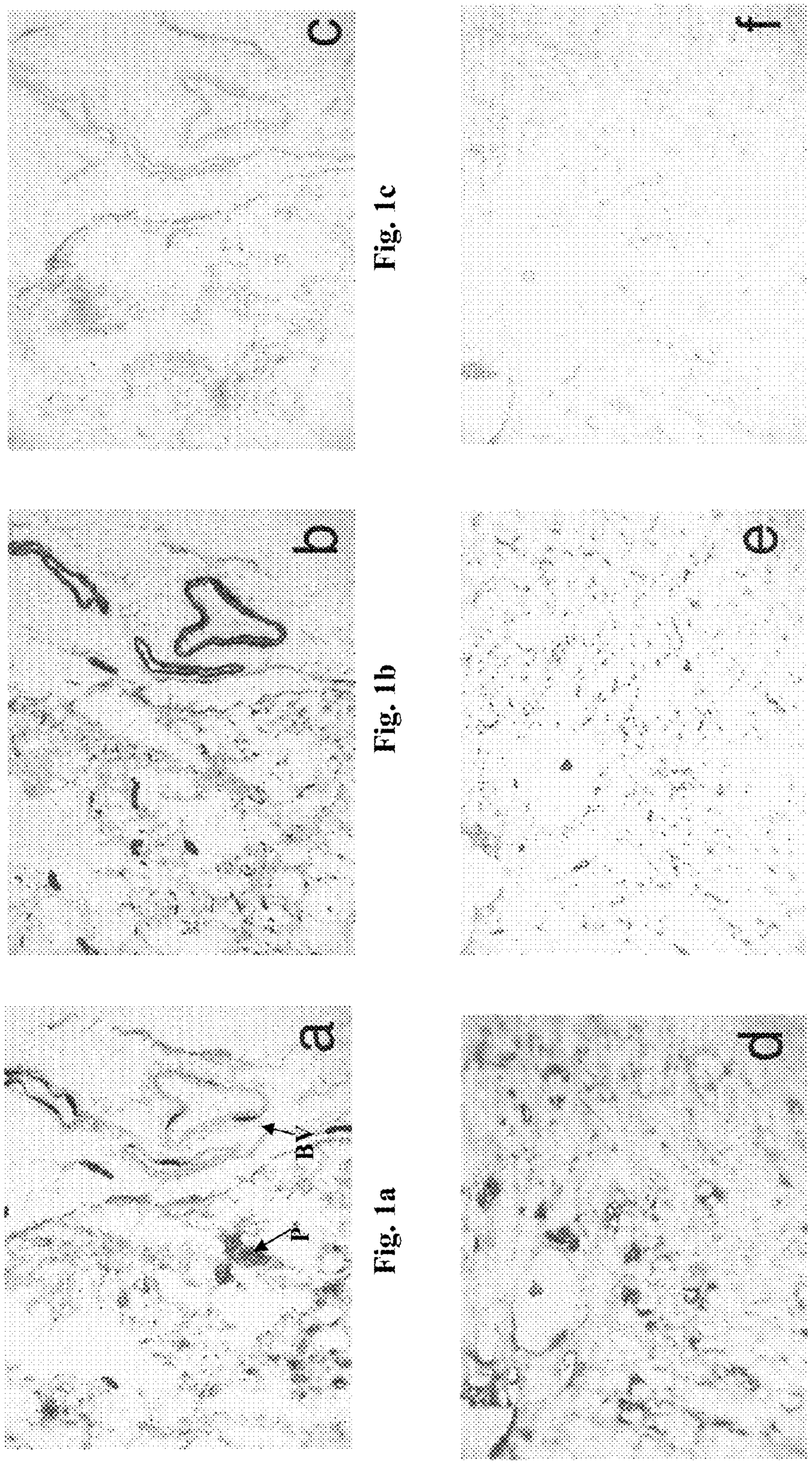
FIGS. 1*a*, 1*b*, 1*c*, 1*d*, 1*e* and 1*f* are photographs showing Immunoperoxidase staining of serial sections from 2 AD brains, using Avidin-Biotinylated Antibody Complex (ABC) method with immune and preimmune sera at 1:100 dilution under 10× magnification.

The present invention relates to an immunogenic composition comprising synthetic peptides capable of inducing antibodies against the main functional/regulatory site of the Aβ peptide with high cross-reactivity both to the soluble $Aβ_{1-42}$ peptide and the plaques in the brain of Alzheimer's Disease (AD) patients. The immunogenic composition when administered to an AD patient or a person predisposed to AD is expected to accelerate the clearance of amyloid plaques and immunoneutralization of the soluble Aβ derived toxins in the brain to prevent and treat AD. In particular, a peptide immunogen of this invention comprises a Th epitope selected from the group consisting of SEQ ID NOS: 1-64 and the immunologically functional analogs thereof linked to a short N-terminal $Aβ_{1-42}$ peptide fragment selected from the group consisting of 10 to 28 amino acid residues comprising EFRH of the $Aβ_{1-42}$ peptide, SEQ ID NO:65, or an immunologically functional analog of the $Aβ_{1-42}$ peptide fragment. Preferably the $Aβ_{1-42}$ peptide fragment is selected from the group SEQ ID NOS: 66-69 or a immunologically functional analogs thereof.

The present invention further provides an immunogenic composition comprising an immunologically effective amount of a peptide composition in a pharmaceutically acceptable vaccine formulation comprising an adjuvant or emulsifier selected from the group consisting of liposyn, saponin, squalene, L121, emulsigen monophosphyryl lipid A (MPL), polysorbate 80, QS21, Montanide ISA51, ISA35, ISA206 and ISA 720 as well as the other efficacious adjuvants and emulsifiers.

The present invention further provides a method for the induction of accelerated clearance of amyloid plaques and immunoneutralization of the soluble Aβ-derived toxins in the brain to prevent and treat Alzheimer Disease in a mammal by administering one or more of the immunogenic peptides to the mammal for a time and under conditions sufficient to induce antibodies directed against the functional/regulatory site of the $Aβ_{1-42}$ peptide. A typical example of a vaccine of the present invention is a peptide composition comprising 5-1000 μg of the peptide immunogen in a vaccine formulated as a water in oil emulsion in a pharmaceutically acceptable adjuvant and/or carrier. A typical method of administering the vaccine is to inject intramuscularly the vaccine formulation at 0.5-2 mL per dose on an immunization schedule of 0, 4, and 8 weeks intervals.

Yet another aspect of the invention relates to an immunogenic synthetic peptide of about 30 to about 60 amino acids consisting of a helper T cell (Th) epitope, linked to an N-terminal $Aβ_{1-42}$ peptide fragment selected from the group consisting of 10 to 28 amino acids with each fragment comprising amino acid residue 1 of the $Aβ_{1-42}$ peptide. See SEQ ID NO:65 wherein D, Aspartic acid, is designated as amino acid residue 1. Preferably the N terminal $Aβ_{1-42}$ peptide fragment is selected from the group SEQ ID NOs: 66-69 or a peptide analog of N-terminal fragment of $A\beta_{1-42}$ peptide. Optionally, amino acid spacers to separate the immunogenic domains may be included. The immunogenic domain elements separated by spacers can be covalently joined in any order provided that either the immunoreactivity of the peptide hapten is substantially preserved or that immunoreactivity to the N-terminal Aβ peptide fragment, soluble $A\beta_{1-42}$ peptide, and the plaques is generated.

An important factor affecting immunogenicity of a synthetic peptide for an N-terminal $A\beta_{1-42}$ fragment immunogen is its presentation to the immune system by T helper cell epitopes (Th). Such Th is most reliably supplied to the peptide immunogen by foreign Th epitopes placed on a separate Th peptide domain element that is extrinsic to the target Aβ peptide. Such peptide immunogens may be produced as hybrid polypeptides by recombinant DNA expression. They may also be more simply and less expensively supplied as a synthetic peptide immunogen comprising the target hapten B cell site from Aβ peptide and T-helper epitopes (Th) appropriate for the host. Such peptides react with helper T-cell receptors and the class II MHC molecules, in addition to antibody binding sites (Babbitt et al., *Nature,* 1985; 317:359) and thus stimulate a tightly site-specific antibody response to the target antibody binding site. Previously such Th was supplied for workable $A\beta_{1-42}$ peptide immunogens by Th intrinsic to aggregated full length Aβ peptide (WO 99/66957; WO 1999/27944; Janus et al., 2000, Morgan et al., 2000) and can be supplied by carrier protein. A wholly synthetic peptide immunogen enjoys the following advantages over $A\beta_{1-42}$ peptide aggregates, carrier conjugates and recombinant polypeptides in that the product is chemically defined for easy quality control. The synthetic peptide immunogen is stable. No elaborate downstream processing nor an elaborate manufacturing facility is needed. The immune response is site-specific and focused on the Aβ target and not the carrier. Thus, undesirable responses such as epitopic suppression are avoided.

Immunogenicity of synthetic N-terminal functional-site directed Aβ peptide immunogens can be optimized by (1) combining N-terminal $A\beta_{1-42}$ peptide fragment with selected foreign promiscuous Th sites to which the majority of a population are responsive; and (2) combining Aβ peptide fragment with Th whose repertoire is enlarged through combinatorial chemistry, and thereby accommodate to the variable immune responsiveness of a genetically diverse population.

It has been found that peptides composition of the present invention are effective in stimulating the production of antibodies against the main functional/regulatory site of the Aβ peptide, with cross-reactivities to the soluble $A\beta_{1-42}$ and the plaques in the brains of AD patients. Based on the immunogenicity data obtained in guinea pigs and baboons, and the data obtained from the immunoperoxidase staining of the amyloid plaques present in human AD brain sections by the specific immune sera obtained, it is expected that the peptide immunogens of the present invention formulated appropriately are effective in humans. It is to be noted that the data obtained in baboons are particularly significant in that this is a species whose immune response closely resemble those of humans.

DETAILED DESCRIPTION OF THE INVENTION

This invention is directed to a novel peptide composition for the generation of high titer polyclonal antibodies with specificity for the main functional/regulatory site of the Aβ peptide, with cross-reactivities to the soluble $A\beta_{1-42}$ and the plaques in the brain of Alzheimer Disease (AD) patients. The antibodies generated by the peptide composition are highly site-specific and bind to the Aβ peptides and to amyloids plaques in the brain. Thus, the present invention provides an effective method for accelerating the clearance of amyloid plaques and immunoneutralization of soluble Aβ derived toxins in the brains for the prevention and treatment of AD.

N-terminal $A\beta_{1-42}$ peptide fragments selected from the group consisting of 10 to 28 amino acids wherein each fragment comprises EFRH of the $A\beta_{1-42}$ peptide (SEQ ID NO:65), are short linear peptides which, by themselves are non-immunogenic. The short $A\beta_{1-42}$ peptide fragments can be immuno-potentiated by chemical coupling to a carrier protein, for example, keyhole limpet hemocyanin (KLH) or by fusion to a carrier polypeptide through recombinant DNA expression, for example, hepatitis B surface antigen. The deficiency of such "Aβ peptide(s)-carrier protein" vaccines is that a major portion of antibodies generated are non-functional antibodies directed against the carrier protein.

The immunogens of the present invention are wholly synthetic peptide immunogens comprising N-terminal fragment of $A\beta_{1-42}$ peptide of 10 to 28 amino acids with each fragment comprising EFRH of the $A\beta_{1-42}$ peptide covalently linked to promiscuous Th epitopes selected from the group consisting of SEQ ID NOs: 1 to 64. The immunogens of the invention elicit the production of site-specific antibodies which bind to the $A\beta_{1-42}$ peptide and its aggregates and are cross reactive with amyloid plaques in the brain to provide for accelerated clearance of amyloid plaques and immunoneutralization of the soluble Aβ-derived toxins in the brain. Thus, the immunogen of the present invention is useful in preventing and treating AD.

The helper T cell epitopes (Th) useful in the invention comprise multiple class II MHC binding motifs. Specific examples of Th covalently linked to an N-terminal $A\beta_{1-42}$ peptide fragment are provided. The results of anti-sera from animals immunized with the immunogen peptides of the present invention demonstrate that potent site-directed Aβ peptide reactive antibodies are generated, in a genetically diverse host population.

Generally, the synthetic immunogenic peptides of the present invention are approximately 20 to 100 amino acids long and comprise:

(i) a helper T cell (Th) epitope selected from the group consisting of SEQ ID Nos: 1 to 64;

(ii) an N-terminal fragment of $A\beta_{1-42}$ peptide from about 10 to about 28 amino acid residues wherein each fragment comprises EFRH of the $A\beta_{1-42}$ peptide; and (iii) optionally a spacer consisting of at least an amino acid to separate the immunogenic domains.

Preferably, the N terminal fragment of the $A\beta_{1-42}$ peptide is selected from the group consisting of SEQ ID NOS: 66-69 and an immunologically effective analog thereof. The Th peptide is covalently attached to either the N- or C-terminus of the target N-terminal fragment of $A\beta_{1-42}$ peptide optionally with a spacer (e.g., Gly-Gly, ε-N Lys).

The peptide immunogen of this invention is represented by one of the following formula:

$(A)_n$-(N-terminal fragment of $A\beta_{1-42}$ peptide)-$(B)_o$—$(Th)_m$—X; or $(A)_n$-$(Th)_m$—$(B)_o$—(N-terminal fragment of $A\beta_{1-42}$ peptide)-X;

wherein each A is independently an amino acid;

each B is a linking group selected from the group consisting of an amino acid, gly-gly, (α, ϵ-N)lys, Pro-Pro-Xaa-Pro-Xaa-Pro (SEQ ID NO:73);

Each Th comprise an amino acid sequence that constitutes a helper T cell epitope, or an immune enhancing analog or segment thereof;

(N-terminal fragment of $A\beta_{1-42}$ peptide) is a synthetic peptide B cell target site antigen and is a fragment of about 10 to about 28 amino acid residues wherein each fragment comprises EFRH of the $A\beta_{1-42}$ peptide or an immunologically functional analog thereof;

X is an α-COOH or α-$CONH_2$ of an amino acid;

n is from 0 to about 10;

m is from 1 to about 4; and o is from 0 to about 10.

The peptide immunogen of the present invention comprises from about 20 to about 100 amino acid residues, preferably from about 25 to about 60 amino acid residues. Preferably, the (N-terminal fragment of $A\beta_{1-42}$ peptide) is selected from the group consisting of SEQ ID Nos: 66-69 and preferably the Th epitope is selected from the group consisting of SEQ ID NOs: 1, 3, 4, 5, 6, 7, 8, 9, 20, 38-40, 47-51 and 52-54. Preferably, m=1, n=1, and o=1 or 2.

When A is an amino acid, it is a non-naturally occurring or naturally occurring amino acid. Non-naturally occurring amino acids include, but are not limited to, ϵ-N lysine, β-alanine, ornithine, norleucine, norvaline, hydroxyproline, thyroxine, γ-amino butyric acid, homoserine, citrulline and the like. Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. When m is greater than one, and two or more of A are amino acids, then each amino acid may independently be the same or different. (A)n may include a spacer, e.g., Gly-Gly, ϵ-N Lys.

B is a spacer and is an amino acid which can be naturally occurring or the non-naturally occurring amino acids as described above. Each B is independently the same or different. The amino acids of B can also provide a spacer, e.g., Gly-Gly, ϵ-Lys, or lysine between the promiscuous Th epitope and the N-terminal fragment of $A\beta_{1-42}$ peptide (e.g., SEQ ID NOs:66-69) or an immunologically functional analog thereof. In addition by physically separating the Th epitope from the B cell epitope, i.e., the N-terminal fragments of $A\beta_{1-42}$ peptide or its immunologically functional analog, the Gly-Gly or ϵ-Lys spacer can disrupt any artifactual secondary structures created by the joining of the Th epitope with an N-terminal fragment of $A\beta_{1-42}$ peptide or its immunologically functional analog and thereby eliminate interference between the Th and/or B cell responses. The amino acids of B can also form a spacer which acts as a flexible hinge that enhances separation of the Th and the N-terminal fragments of $A\beta_{1-42}$ peptide. Examples of sequences encoding flexible hinges are found in the immunoglobulin heavy chain hinge region. Flexible hinge sequences are often proline rich. One particularly useful flexible hinge is provided by the sequence Pro-Pro-Xaa-Pro-Xaa-Pro (SEQ ID NO:77), where Xaa is any amino acid, and preferably aspartic acid. The conformational separation provided by the amino acids of B permits more efficient interactions between the presented peptide immunogen and the appropriate Th cells and B cells to enhances the immune responses to the Th epitope and the antibody-eliciting epitope or their immunologically functional analogs.

Th is a sequence of amino acids (natural or non-natural amino acids) that comprises a Th epitope. A Th epitope may be a continuous or discontinuous epitope. In a discontinuous Th epitope, not every amino acid of Th is necessary. A Th epitope, or an analog or fragment thereof, is capable of enhancing or stimulating an immune response to the N-terminal fragment of $A\beta_{1-42}$ peptide. Th epitopes that are immunodominant and promiscuous are highly and broadly reactive across animal and human populations with widely divergent MHC types (Partidos et al., 1991; U.S. Pat. No. 5,759,551). The Th epitope of the subject peptides is about 10 to about 50 amino acids, preferably from about 10 to about 30 amino acids. When multiple Th epitopes are present (i.e., $m \geqq 2$), each Th epitope may be the same or different. A Th segment comprises a contiguous portion of a Th epitope that is sufficient to enhance or stimulate an immune response to the N-terminal fragment of $A\beta_{1-42}$ peptide.

Th epitopes of the present invention include those derived from foreign pathogens including but not limited to those exemplified in Table 1 (SEQ ID Nos:1-21). Further, Th epitopes include idealized artificial Th and artificial idealized combinatorial Th disclosed in WO 99/66957 and listed here in Table 2 as SEQ ID Nos 22-64. Peptides comprising combinatorial Th are produced simultaneously in a single solid-phase peptide synthesis in tandem with the N-terminal fragment of $A\beta_{1-42}$ peptide, A and B. The Th epitopes also include immunologically functional analogs thereof, having conservative substitutions, additions, deletions and insertions therein of from one to about 10 amino acid residues as long as the Th-stimulating function has not been essentially modified.

In the synthetic peptides of this invention, the Th epitope is covalently attached through a spacer B to either the N terminus or C terminus of the N-terminal fragment of $A\beta_{1-42}$ peptide or an immunologically functional analog thereof. An immunologically functional analog of the N-terminal fragment of $A\beta_{1-42}$ peptide may comprise conservative substitutions, additions, deletions, or insertions of from one to about four amino acid residues as long as immune responses that are crossreactive with the $A\beta_{1-42}$ peptides are elicited. The conservative substitutions, additions, and insertions can be accomplished with natural or non-natural amino acids as defined above.

The preferred peptide immunogens of this invention are those comprising the N-terminal fragment of the $A\beta_{1-42}$ peptide fragments selected from the group consisting of SEQ ID NOs: 66-69 or an immunologically functional analog thereof; a spacer (e.g., Gly-Gly, ϵ-Lys); a Th epitope selected from the group consisting of an HBs Th (SEQ ID NO:1); HBc Th (SEQ ID NO:20); MVF Th (SEQ ID NOS:8, 9); PT Th (SEQ ID NOs:4, 5, 7), TT Th (SEQ ID NOs:3, 4, 6); CT Th (SEQ ID NOs:12, 21); DT Th (SEQ ID NO:13, 14), MVF Th derived artificial Th selected from the group consisting of SEQ ID Nos:38-40, 47-51); HBV Th derived artificial Th selected from the group consisting of SEQ ID NOS: 52-54. See Tables 1 and 2.

Peptide compositions which contain a cocktail of the subject peptide immunogens with two or more Th epitopes may enhance immunoefficacy in a broader population and thus provide an improved immune response to the $A\beta_{1-42}$ peptides and their fragments.

The peptide immunogens of this invention can be made by chemical synthesis methods which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH2 protected by either t-Boc or F-moc chemistry using side chain protected amino acids on, for example, an Applied Biosystems Peptide Synthesizer Model 430A or 431. Preparation of peptide constructs comprising combinatorial library peptides for Th epitopes can be accomplished by providing a mixture of alternative amino acids for coupling at a given variable position. After complete assembly of the desired peptide immunogen, the resin is treated according to standard procedures to cleave the peptide from the resin and deblock the functional groups on the amino acid side chains. The free peptide is purified by HPLC and characterized biochemically, for example, by amino acid analysis or by sequencing. Purification and characterization methods for peptides are well known to one of ordinary skill in the art.

The immunogen of the present invention may also be prepared as a branched polymer by synthesis of the desired peptide construct directly onto a branched poly-lysyl core resin (Wang, et al., Science, 1991; 254:285-288).

Alternatively, the longer synthetic peptide immunogens can be synthesized by well known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The efficacy of the peptide composition of the present invention can be established by injecting an animal, for example, guinea pigs, with an immunogenic composition comprising peptides of the invention. See, Table 4, SEQ ID NOS:70-75. The humoral immune response to the N-terminal fragment of $A\beta_{1-42}$ peptide and the soluble $A\beta_{1-42}$ peptide are monitored. A detailed description of the procedures used is provided in the Examples herein below.

Another aspect of this invention provides a peptide composition comprising an immunologically effective amount of one or more of the peptide immunogens of this invention in a pharmaceutically acceptable delivery system. Accordingly, the subject peptide composition can be formulated as a vaccine using pharmaceutically acceptable adjuvants, carriers or other ingredients routinely employed in the formulation of vaccines. Among the ingredients that can be used in this invention are adjuvants or emulsifiers including alum, liposyn, saponin, squalene, L121, emulsigen monophosphyryl lipid A (MPL), polysorbate 80, QS21, Montanide ISA51, ISA35, ISA206 and ISA 720 as well as the other efficacious adjuvants and emulsifiers. The composition may be formulated for immediate release or sustained release. The composition may also be formulated for induction of systemic immunity, e.g., by entrapment in or coadministration with microparticles. Such formulations are readily available to one of ordinary skill in the art.

The immunogens of the present invention can be administered via any conventional route, such as subcutaneous, oral, intramuscular, parenteral or enteral route. The immunogens can be administered in a single dose or in multiple doses. A suitable immunization schedule is readily determined and available to one of ordinary skill in the art.

The peptide composition of the present invention comprises an effective amount of one or more of the peptide immunogens of the present invention and a pharmaceutically acceptable carrier. Such a composition in a suitable dosage unit form generally contains about 0.25 μg to about 500 μg of the immunogen per kg body weight. When delivered in multiple doses, the effective amount may be conveniently divided per dosage unit. For example, an initial dose, e.g. 0.0025-0.5 mg per kg body weight; preferably 1-50 μg per kg of body weight of the peptide immunogen is to be administered by injection, preferably intramuscularly, followed by repeat (booster) doses of a similar amount. Dosage will depend on the age, weight and general health of the subject as is well known in the vaccine and therapeutic arts.

The immune response of the synthetic $A\beta_{1-42}$ peptide immunogens can be improved by delivery through entrapment in or on biodegradable microparticles of the type described by O'Hagan et al. (Vaccine, 1991; 9: 768-771). The immunogens can be encapsulated with or without an adjuvant in biodegradable microparticles, to potentiate immune responses, and to provide time-controlled release for sustained or periodic responses, and for oral administration, (O'Hagan et al., 1991; and, Eldridge et al., 1991; 28: 287-294).

The following examples are provided to illustrate the invention. The scope of the invention is not to be limited to the specific peptide immunogens and compositions provided. The examples demonstrate that the peptide immunogens of the present invention are useful for eliciting site-directed antibodies to both $A\beta_{1-10}$ and $A\beta_{1-14}$ fragments as well as cross-reactive antibodies to soluble $A\beta_{1-42}$ peptides as early as 4 weeks after the initial immunization.

EXAMPLE 1

Typical Methods to Synthesize Aβ Peptide Immunogens of the Present Invention Peptide immunogens listed in Table 4 (SEQ ID NOS:70-76) were synthesized individually by the Merrifield solid-phase synthesis technique on Applied Biosystems automated peptide synthesizers (Models 430, 431 and 433A) using Fmoc chemistry. Preparation of peptide immunogens comprising a combinatorial library Th, i.e., idealized artificial Th site such as MvF derived Th1-8 (SEQ ID NOs:38-40), can be accomplished by providing a mixture of the desired amino acids for chemical coupling at a given position as specified in the design. After complete assembly of the desired peptide, the resin was treated according to standard procedure using trifluoroacetic acid to cleave the peptide from the resin and deblock the protecting groups on the amino acid side chains. The cleaved, extracted and washed peptides were purified by HPLC and characterized by mass spectrometry and reverse phase HPLC.

EXAMPLE 2

Evaluation of the Immunogenicity of the Aβ Peptide Immunogens of the Present Invention Aβ-derived peptide immunogens were evaluated on groups of guinea pigs as specified by the experimental immunization protocol outlined below and by serological assays for determination of immunogenicity.

Standard Experimental Design:

Immunogens: (1) individual peptide immunogen; or (2) a mixture of equal molar peptide immunogens as specified in each example.

Dose: 100 μg in 0.5 mL per immunization unless otherwise specified

Route: intramuscular unless otherwise specified

Adjuvants: Complete Freund's Adjuvant (CFA)/Incomplete Adjuvant (IFA); or other water in oil emulsions otherwise specified. CFA/IFA groups received CFA week 0, IFA in subsequent weeks.

Dose Schedule: 0, 3, and 6 weeks or otherwise specified.

Bleed Schedule: weeks 0, 5, 8 or otherwise specified

Species: Duncan-Hartley guinea pigs or otherwise specified

Assay: Specific ELISAs for each immune serum's anti-peptide activity. The solid phase substrate was the Aβ peptide fragment e.g. $Aβ_{1-14}$ or full length $Aβ_{1-42}$ (SEQ ID NOs: 67 and 65). Blood was collected and processed into serum, and stored prior to ELISA with the target peptides.

The immunoreactivities of the antibodies elicited against Aβ peptides and against the soluble $Aβ_{1-42}$ peptides were determined by ELISAs (enzyme-linked immunosorbent assays) using 96-well flat bottom microtiter plates which were coated with the $Aβ_{1-42}$ peptide fragments, SEQ ID NOs: 67 or 65 as the immunosorbent. Aliquots (100 μL) of the peptide immunogen solution at a concentration of 5 μg/mL were incubated for 1 hour at 37° C. The plates were blocked by another incubation at 37° C. for 1 hour with a 3% gelatin/PBS solution. The blocked plates were then dried and used for the assay. Aliquots (100 μL) of the test immune sera, starting with a 1:100 dilution in a sample dilution buffer and ten-fold serial dilutions thereafter, were added to the peptide coated plates. The plates were incubated for 1 hour at 37° C.

The plates were washed six times with 0.05% PBS/Tween® buffer. 100 μL of horseradish peroxidase labeled goat-anti-species specific antibody was added at appropriate dilutions in conjugate dilution buffer (Phosphate buffer containing 0.5M NaCl, and normal goat serum). The plates were incubated for 1 hour at 37° C. before being washed as above. Aliquots (100 μL) of o-phenylenediamine substrate solution were then added. The color was allowed to develop for 5-15 minutes before the enzymatic color reaction was stopped by the addition of 50 μL 2N $H_2SO_4$. The $A_{492\ nm}$ of the contents of each well was read in a plate reader. ELISA titers were calculated based on linear regression analysis of the absorbances, with cutoff $A_{492\ nm}$ set at 0.5. The cutoff value chosen was rigorous with the values for diluted normal control samples being less than 0.15.

EXAMPLE 3

Characterization of the Relative Immunogenicities of $Aβ_{1-42}$ and its N-Terminal Fragments for Optimization of Design for Site-Directed Aβ Peptide-Based Synthetic Vaccine To design a total synthetic vaccine that generates a high level of high affinity antibodies against the Aβ peptides with high cross-reactivity to the soluble $Aβ_{1-42}$ peptides and the plaques in the brain of AD patients, the relative immunogenicities of $Aβ_{1-42}$ and its N-terminal fragments were characterized initially. In order to determine the relative immunological properties of the various regions within $Aβ_{1-42}$ peptide, a mild adjuvant suitable for human use, alum was employed in the first study. The relative immunogenicities of $Aβ_{1-42}$ peptide and an N-terminal fragment thereof, $Aβ_{1-28}$ were compared. The immunogenicity evaluation was conducted according to procedures described in Example 2. Unexpectedly, $Aβ_{1-28}$ was found to be more immunogenic than the $Aβ_{1-42}$ peptide, indicating that there is immunosuppression within C-terminal fragment $Aβ_{29-42}$ (Table 5).

Subsequently, the immunogenicity of $Aβ_{1-28}$ was compared to $Aβ_{1-14}$, a shorter N-terminal fragment of $Aβ_{1-42}$. A more potent adjuvant suitable for human use (Montanide ISA51, Seppic, Paris, FR) was employed for the preparation of a water-in-oil emulsion for formulating the vaccine. Based on the data obtained as shown in Table 6, the relative immunogenicities for the three Aβ peptides (i.e. $Aβ_{1-14}$, $Aβ_{1-28}$ and $Aβ_{1-42}$) were ranked $Aβ_{1-28}$>$Aβ_{1-42}$>$Aβ_{1-14}$. Surprisingly, the loss of the C-terminal 14 mer from $Aβ_{1-42}$, improved rather than reduced the immunogenicity. The antibody response against Aβ is primarily directed to the N-terminal region, particularly the $Aβ_{1-14}$ N-terminal fragment as shown by ELISA data (Table 6). However, a further shortening of the $Aβ_{1-28}$ fragment from the C-terminal to form the $Aβ_{1-14}$ fragment resulted in a loss in immunogenicity.

The short $Aβ_{1-14}$ fragment contains the main functional/regulatory site, EFRH, located at positions 3-6 of the $Aβ_{1-42}$ peptide as reported by Solomon et al. The blocking of this epitope by antibodies modulates the dynamics of aggregation as well resolubilization of already formed aggregates (Soloman et al., *Proc Natl Acad. Sci,* 1996; 93:452-455; *Proc Natl Aca. Sci,* 1997; 94:4109-4112). Most of the anti-$Aβ_{1-28}$ and $Aβ_{1-42}$ antibodies are directed against the N-terminal fragment of the $Aβ_{1-42}$ peptide containing this epitope (Table 6). However, the $Aβ_{1-14}$ fragment by itself was poorly immunogenic. The results of this experiment suggest the presence of an intrinsic Th epitope within the $Aβ_{15-28}$ segment. This intrinsic Th epitope accounts for the modest immunogenicities of $Aβ_{1-28}$ and $Aβ_{1-42}$ peptides in guinea pigs.

The presence of a Th epitope in the $Aβ_{15-28}$ fragment is desirable. However, it is desirable to be able to engineer a more potent immunogen for a successful human vaccine when faced with the limitation of a restricted human MHC molecule, the number of appropriate doses and the type of adjuvants permitted for human use. Therefore, we attempted the linkage of a foreign or extrinsic Th such as that derived from HBV Th (SEQ ID NO: 1) to the C-terminal of the $Aβ_{1-28}$ peptide (SEQ ID NO:66). The extrinsic Th epitope significantly enhanced the immunogenicity of the $Aβ_{1-28}$ fragment as shown in Table 6. The antibody response to the engineered immunogen with the $Aβ_{1-28}$ fragment remained directed to the functional N-terminal fragment of peptide immunogen (SEQ ID NO: 70) making this construct a better immunogen than the $Aβ_{1-28}$ fragment or $Aβ_{1-42}$ fragment alone. This peptide immunogen (SEQ ID NO: 70) represents a peptide immunogen with the formula:

$$(A)_n\text{(N-terminal fragment of Aβ peptide)}-(B)_o—(Th)_m$$

wherein:

A is $αNH_2$, with $Aβ_{1-28}$ being an N-terminal fragment of $Aβ_{1-42}$;

B is glycine;

Th is a helper T cell epitope derived from a foreign pathogen,

HBsAg Th (SEQ ID NO: 1), and wherein n is 1, m is 1 and o is 2.

EXAMPLE 4

Lower Limit of N-Terminal Fragment of Aβ for the Development of Aβ Based Synthetic Vaccine for AD Since the main functional/regulatory site comprising the EFRH residues is located at positions 3-6 of the $Aβ_{1-42}$ peptide (Soloman et al. *Proc Natl Acad. Sci,* 1996; 93:452-455; *Proc Natl Aca. Sci,* 1997; 94:4109-4112), it was useful to explore the shortest N-terminal fragment of $A\beta_{1-42}$ peptide as an optimal B cell target site on Aβ for incorporation into the synthetic immunogen of the present invention.

Each of several short non-immunogenic N-terminal fragments of Aβ, $A\beta_{1-10}$, $A\beta_{1-12}$, $A\beta_{1-14}$ along with $A\beta_{1-28}$ was incorporated into immunogens designed with a representative idealized artificial Th (SEQ ID NO:51). Linkage was through an εN-Lys spacer. The engineered constructs were formulated with strong adjuvants due to the expected low immunogenicity of the short Aβ fragments. The three synthetic constructs were formulated in complete and incomplete Freund's adjuvant and tested for their immunogenicities based on procedures as described in Example 2. As shown in Table 7, all four peptide immunogens were highly immunogenic with $Log_{10}$ ELISA titers in the range from 4.3 to 5.6 (i.e. $10^{4.3}$ to $10^{5.6}$) with very high crossreactivities to the full length $A\beta_{1-42}$ peptide after only four weeks from the initial immunization. More importantly, fragments as small as $A\beta_{1-10}$, $A\beta_{1-12}$ and $A\beta_{1-14}$ each linked to the idealized artificial Th (SEQ ID NO:51) were found to be highly immunogenic after linkage to the disclosed artificial Th epitope (Table 7). These peptide immunogens were designed in accordance with the formula:

$(A)_n$-(N-terminal fragment of Aβ peptide)-$(B)_o$—$(Th)_m$ wherein:

A is $\alpha NH_2$, wherein the N-terminal fragment is $A\beta_{1-10}$, $A\beta_{1-12}$, $A\beta_{1-14}$ or $A\beta_{1-28}$;

B is ε-N Lysine, a spacer linked through its epsilon amino group to the next amino acid;

Th is a helper T cell epitope derived from an idealized artificial Th, MVF Th1-16 (SEQ ID NO:51), wherein n is 1, m is 1 and o is 1.

It was found that further reduction in the length of the N-terminal fragment of Aβ to less than a 10 mer would result in more limited, thus undesirable, immunogenicity. It appears that peptides smaller than 10 amino acids are problematic for receptor recognition by class II MHC molecules (*Immunology*, Fifth edition, ed. Roitt et al., 1998, Mosby International Ltd., London, pp 88-89).

Based on this study of Aβ, the useful B cell site derived from $A\beta_{1-42}$ should be in the size range of about 10 to about 28 residues.

EXAMPLE 5

Site-Directed Immunoreactivity Targeted by the Synthetic Peptide Immunogen Linked to Artificial Th Epitope The non-immunogenic N-terminal fragment such as $A\beta_{1-14}$ of Aβ peptide was linked either through an εN-lysine spacer to an artificial Th peptide designated as MVF Th 1-16 (SEQ ID NO:51), or through a standard chemical coupling procedure to a conventional carrier protein KLH. The two immunogenic constructs were evaluated in guinea pigs for their relative "site-directed" immunogenicities to Aβ peptide and the resultant respective reactivity of the antibodies towards their respective carriers, the artificial Th epitope or the KLH carrier protein, according to the procedures described in Example 2. The short $A\beta_{1-14}$ peptide alone as a control immunogen, and the two immunogenic constructs were formulated in a water-in-oil emulsion containing the adjuvant ISA51, a formulation that is suitable for human use.

As shown in Table 8, the N-terminal $A\beta_{1-14}$ fragment by itself is non-immunogenic as expected. The synthetic immunogen comprising $A\beta_{1-14}$ fragment and artificial Th (SEQ ID NO: 73) was found to be highly immunogenic in eliciting site-directed antibodies to $A\beta_{1-14}$. The antibodies were also found to be highly cross-reactive to soluble $A\beta_{1-42}$ peptide as early as 4 weeks after the initial immunization ($Log_{10}$ titers of 4.094 and 4.126 for 4 and 6 weeks post initial immunization respectively). When these Aβ-reactive high titer immune sera were tested by ELISA on the MVF Th1-16 peptide (SEQ ID NO 51) coated plate, they were found to be negative ($Log_{10}$ titer of 0.038 and 0.064 for 4 and 6 weeks post initial immunization respectively) showing that irrelevant antibodies were not produced. The data obtained as shown in Table 8 clearly demonstrated the highly specific site-directed characteristic of the peptide immunogen of the present invention.

The immunogen with the carrier protein KLH was found to be highly immunoreactive with the conventional peptide-carrier protein conjugate (e.g. $Log_{10}$ titers of 4.903 and 5.018 for 4 and 6 weeks post initial immunization respectively). However, the antibodies elicited were only moderately cross-reactive with the soluble $A\beta_{1-42}$ peptide (e.g. with $Log_{10}$ titers of 3.342 and 2.736 for 4 and 6 weeks post initial immunization respectively). This is approximately 10× to 100× less than SEQ ID NO:73. Unexpectedly, the peptide immunogens of the present invention were highly site-directed and focused. Only functionally important antibodies towards the anti-aggregation and disaggregation sites on the N-terminal fragment of the Aβ peptide were generated rather than towards irrelevant carrier sites.

EXAMPLE 6

Evaluation of Aβ Peptide Immunogen by Cross-Reactivities to Senile Plaques

Brains of AD patients with plaques and tangles and thioflavine S positive blood vessels (TSBV) containing amyloid plaques were used for evaluation of cross-reactivities to polymeric senile plaques of the immune sera raised in guinea pigs and baboons against Aβ peptide immunogens. Plaques and TSBV reactivities were detected by immunoperoxidase staining using Avidin-Biotinylated antibody Complex (ABC) method or by immunofluorescence staining using rhodamine conjugated Fab fragment of species specific anti-IgG. All guinea pig sera were tested at a dilution of 1:100 with end point titers determined for some of the samples. All baboon sera were tested at a dilution of 1:50. The evaluation of the immune and preimmune sera were kindly performed under code by Dr. Gaskin as described (Gaskin et al., *J. Exp Med.* 165:245, 1987).

In FIG. 1, serial cross sections of brains from 2 AD patients were initially examined at 10× magnification. Sections (a), (b) and (c) are from AD Brain 1 and (d), (e) and (f) are from AD brain 2. Preimmune normal serum and immune sera from guinea pigs collected at 6 weeks post-initial immunization were tested by immunoperoxidase staining on cryostat sections from AD temporal cortex rich in plaques and neurofilament tangles (NFT). The immune sera used in the first study shown on slides FIGS. 1*a* and 1*d* were obtained from animals immunized with $A\beta_{1-28}$-εK-MvF Th1-16 (SEQ ID NO:74) prepared in ISA51 water-in-oil emulsion. The results show significant binding to both senile plaques and amyloid plaques on the thioflavine S positive blood vessels (TSBV). The cross-reactivities of the immune sera raised against the equivalent immunogen prepared in CFA/ICFA are shown in slides FIGS. 1*b* and 1*d*. Unexpectedly, in contrast to the results obtained with the vaccine formulated with ISA51, preferential binding to the $A\beta_{1-28}$ plaques on the blood vessels (TSBV) were observed for the sera raised against the CFA/ICFA vaccine. This means that the antibodies elicited by the vaccine formulated with ISA51 is distinguishable from the antibodies raised by the vaccine formulated in CFA/ICFA. Moreover, the antibodies generated by the vaccines formulated according to the present invention provided antibodies that have the desired higher cross reactivity to senile plaques in the brain tissue. Preimmune serum gave no staining in corresponding serial sections shown in slides FIGS. 1*c* and 1*f*.

Further Immunoperoxidase staining of serial cross sections of AD brain 1 with preimmune and immune sera at 1:100 dilution are shown in FIGS. 2*a* to 2*e* at 40× magnification. The sera obtained from animals immunized with $A\beta_{1-28}$-εK-MVF Th 1-16 (Seq ID NO:74) prepared in ISA 51 water-in-oil emulsion strongly stained the plaques forming a pattern of cores as shown in slides FIGS. 2*a* and 2*d*. Again, surprisingly, staining with immune sera prepared against the corresponding CFA/ICFA formulation gave a different staining pattern in that reactivities with plaques were predominantly on the blood vessels as shown in FIG. 2*b* rather than with the plaques in the brain tissue. Preimmune serum did not stain the sections as shown in FIG. 2*c*. The hyperimmune sera generated by immunization with $A\beta_{1-42}$ peptide alone in CFA/ICFA, despite its strong reactivities with $A\beta_{1-28}$ by ELISA, gave a surprisingly weak staining pattern in the section shown in FIG. 2*e*.

Similar immunostaining of AD brain tissue was performed with 11 pooled immune and preimmune sera obtained from guinea pigs immunized with the various vaccine formulations described in Examples 3, 4 and 5. These sera were also evaluated for their antibody reactivities with the functional-site by $A\beta_{1-14}$ ELISA, and with the soluble $A\beta_{1-42}$ by $A\beta_{1-42}$ ELISA (Table 9). In general, parallel trends were found with sera tested in all three assays. As shown in Table 9, the anti-peptide reactivities of the pre-immune serum and the sera raised against the short peptide $A\beta_{1-14}$ alone formulated in ISA51 water-in-oil emulsion by ELISA were low and the cross-reactivities to plaques were negligible. Modest reactivities were found with sera from animals vaccinated with $A\beta_{1-28}$ peptide alone formulated in Alum and in ISA51, and $A\beta_{1-14}$ conjugated to KLH and formulated in ISA51. Whereas, significant site-directed reactivities to the functional $A\beta_{1-14}$ site, to soluble Aβ, and to the plaques and TSBV in AD patient brain tissue sections were found with sera from animals immunized with synthetic Aβ/Th immunogens of the present invention. The results obtained from these studies, therefore, demonstrate excellent and useful immunogenicity of the peptide immunogens comprising the N-terminal fragment of $A\beta_{1-42}$ having amino acids from 1-28 to about 1-10, linked to foreign Th epitopes. Moreover, the results showed that the presence of a foreign Th epitope improves the immunogenicity of the peptide immunogens of the present invention to a surprising extent. The peptide immunogens of the present invention in clinically acceptable vaccine formulations acceptable to use in humans generated antibodies having the desired cross-reactivity to senile plaques in the brain tissues of AD patients.

EXAMPLE 7

The Immunogenicity of Representative Aβ Peptide Vaccines in Baboons as Predictor of Immunotherapeutic Efficacy for AD A representative synthetic immunogen, $A\beta_{1-28}$-ε-K-MvF Th1-16 (SEQ ID NO:74), formulated in ISA51 water-in-oil emulsion at dose levels of 25 μg/0.5 mL, 100 μg/0.5 mL and 400 μg/0.5 mL were given to three baboons Y299, X398, X1198 at 0, 3 and 6 weeks schedule from initial immunization. Pre-immune sera and sera at weeks 5 and 8 weeks post initial immunization (wpi) were collected. For comparison, a fourth baboon X798 was given 100 μg/0.5 mL doses of an equimolar mixture of free peptides $A\beta_{1-28}$ and $A\beta_{1-42}$ formulated in alum, the standard adjuvant approved for human use. Preimmune sera were used as the negative control.

Sera from all four immunized animals were collected and evaluated for their antibody reactivities with the functional site by $A\beta_{1-14}$ ELISA, and for reactivities with soluble $A\beta_{1-42}$ by $A\beta_{1-42}$ ELISA (for sera collected at 0, 5 and 8 wpi). The cross-reactivities of the anti-sera (8 wpi only) with the senile plaques and the plaques in thioflavine S positive blood vessels were evaluated by immunostaining as described in Example 6. Instead of using anti-baboon Ig, the antibody detector used is an Fab fragment from anti-human IgG that recognizes all human isotypes and is cross-reactive with baboon IgG.

Parallel trends again were found with sera tested in all three assays. As shown in Table 10, pre-immune sera were negative. Modest ELISA reactivities were found with serum from animal X798 vaccinated with $A\beta_{1-28}$ and $A\beta_{1-42}$ formulated in Alum. However, the reactivity of this serum was weak for the recognition of senile plaques. In contrast, significant site-directed reactivities to the functional-site of $A\beta_{1-14}$, to soluble $A\beta_{1-42}$, and to the plaques and TSBV in AD patient brain sections were found with sera collected at 8 weeks post initial immunization from animals immunized with the representative composition of the invention (SEQ ID NO:74) at both the 100 μg/0.5 mL and 400 μg/0.5 mL doses formulated with ISA51. The results obtained from this baboon study, therefore, demonstrated the usefulness of the immunogen of the present invention in a vaccine formulation appropriate for humans. The improvement in immunogenicity (10 to 100× increase in specific antibody titers to the functional-site of Aβ) is very significant in comparison to the peptide vaccine of the prior art with the immune responsiveness in baboons closely resembling that of humans.

Similarly, a mixture containing two to three synthetic immunogens of the present invention can be used for formulation into vaccines at from about 25 to 1000 μg per dose to elicit functional anti-$A\beta_{1-14}$ antibodies in genetically diverse human populations for the prevention and treatment of AD. Broad immunogenicity in humans is expected due to the presence of a promiscuous Th epitope in the peptide immunogen of the invention that provides for achieving broad MHC recognition.

TABLE 1

Pathogen-derived Promiscuous T Helper Cell Epitopes (Th)

| Description of Th | Amino Acid Sequence | SEQ ID NO |
|---|---|---|
| HBs Th[a] | FFLLTRILTIPQSLD | 1 |
| $PT_1$ Th[a] | KKLRRLLYMIYMSGLAVRVHVSKEEQYYDY | 2 |
| $TT_1$ Th[a] | KKQYIKANSKFIGITEL | 3 |
| $TT_2$ Th[a] | KKFNNFTVSFWLRVPKVSASHL | 4 |
| $PT_{1A}$ Th[a] | YMSGLAVRVHVSKEE | 5 |
| $TT_3$ Th[a] | YDPNYLRTDSDKDRFLQTMVKLFNRIK | 6 |
| $PT_2$ Th[a] | GAYARCPNGTRALTVAELRGNAEL | 7 |

TABLE 1-continued

Pathogen-derived Promiscuous T Helper Cell Epitopes (Th)

| Description of Th | Amino Acid Sequence | SEQ ID NO |
|---|---|---|
| $MVF_1$ Th[a] | LSEIKGVIVHRLEGV | 8 |
| $MVF_2$ Th[a] | GILESRGIKARITHVDTESY | 9 |
| $TT_4$ Th[a] | WVRDIIDDFTNESSQKT | 10 |
| $TT_5$ Th[a] | DVSTIVPYIGPALNHV | 11 |
| CT Th[a] | ALNIWDRFDVFCTLGATTGYLKGNS | 12 |
| DT1 Th[a] | DSETADNLEKTVAALSILPGHGC | 13 |
| DT2 Th[a] | EEIVAQSIALSSLMVAQAIPLVGELVDIGF AATNFVESC | 14 |
| PF Th[a] | DHEKKHAKMEKASSVFNVVNS | 15 |
| SM Th[a] | KWFKTNAPNGVDEKHRH | 16 |
| $TraT_1$ Th[a] | GLQGKHADAVKAKG | 17 |
| $TraT_2$ Th[a] | GLAAGLVGMAADAMVEDVN | 18 |
| $TraT_3$ Th[a] | STETGNQHHYQTRVVSNANK | 19 |
| $HB_{c50-69}$[b] | SDFFPSVRDLLDTASALYRE | 20 |
| $CTP_{11}$ Th[c] | TINKPKGYVGKE | 21 |

[a]U.S. Pat. No. 5,759,551
[b]Ferrari et al., J Clin Invest, 1991; 88:214
[c]Stagg et al., Immunology, 1993; 71:1

TABLE 2

Artificial Idealized Th and Combinatorial Library Idealized Artificial Th

| Th Identifier | Amino Acid Sequence | SEQ ID NO |
|---|---|---|
| a. MVF Th and Th epitopes derived therefrom | | |
| MVF TM | LSEIKGVIVHRLEGV | 22 |
| SSAL1 Th1 | DLSDLKG**LLL**HKLDGL | 23 |
| | EISEIRG**III**HRIEGI | 24 |
| | EVSEVRG**VVV**HRVEGV | 25 |
| | EFSEFRG**FFF**HRFEGF | 26 |
| MVF Th1-1 | ISEIKGVIVHKIEGI | 27 |
| | MTSERTVIVTRMETM | 28 |
| | LTEIKGVIVHKLEGI | 29 |
| MVF Th1-2 | ISEIKGVIVHKIEGI | 30 |
| | ITEIRTVIVTRIETI | 31 |
| MVF Th1-3 | MSEIKGVIVHKLEGM | 32 |
| | LTEMRTVIVTRMETV | 33 |
| MVF Th1-4 | ISEIKGVIVHKIEGI | 34 |
| MVF Th1-5 | ITEIRTVIVTRIETI | 35 |
| MVF Th1-6 | MSEMKGVIVHKMEGM | 36 |
| MVF Th1-7 | LTEIRTVIVTRLETV | 37 |
| MVF Th1-8 | ISISEIKGVIVHKIEGILF | 38 |
| | ISMTEIRTVIVTRMETMLF | 39 |
| | ISLSEIKGVIVHKLEGVLF | 40 |

TABLE 2-continued

Artificial Idealized Th and Combinatorial Library Idealized Artificial Th

| Th Identifier | Amino Acid Sequence | SEQ ID NO |
|---|---|---|
| MVF Th1-9 | ISISEIKGVIVHKIEGILF | 41 |
| | ISITEIRTVIVTRIETILF | 42 |
| MVF Th1-10 | ISLSEIKGVIVHKLEGMLF | 43 |
| | ISMTEMRTVIVTRMETVLF | 44 |
| MVF Th1-11 | ISLTEIRTVIVTRLETVLF | 45 |
| MVF Th1-12 | ISITEIRTVIVTRIETILF | 46 |
| | ISISEIKGVIVHKIEGILF | 47 |
| MVF Th1-13 | ISITEIRTVIVTRIETILF | 48 |
| MVF Th1-14 | ISMSEMKGVIVHKMEGMLF | 49 |
| MVF Th1-15 | ISLTEIRTVIVTRLETVLF | 50 |
| MVF Th1-16 | ISITEIKGVIVHRIETILF | 51 |
| b. HBsAg Th, Prototype and Derivatives | | |
| HbsAg-Th1 | FFLLTRILTIPQSLD | 52 |
| HbsAg-Th1-1 | KKKFFLLTRILTIPQSLD | 53 |
| HbsAg-Th1-2 | FFLLTRILTIPQSL | 54 |
| SSAL2 Th2 | KKKLF**LL**TK**LL**TLPQSLD | 55 |
| | RRRIK**II**TR**II**TIPLSIR | 56 |
| | KKKVR**VV**TK**VV**TVPISVD | 57 |
| | KKKFF**FF**TK**FF**TFPVSFD | 58 |
| | KKKLF**LL**TK**LL**TLPFSLD | 59 |
| HbsAg Th1-3 | KKKIITITRIITIITTID | 60 |
| HbsAg Th1-4 | KKKIITITRIITIITTI | 61 |
| HbsAg Th1-5 | KKKMMTMTRMITMITTID | 62 |
| HbsAg Th1-6 | FITMDTKFLLASTHIL | 63 |
| HbsAg Th1-7 | KKKFITMDTKFLLASTHIL | 64 |

TABLE 3

Amino Acid Sequences of $A\beta_{1-42}$ Peptides and its N-terminus Fragments

| SEQ ID NO | | Amino Acid Sequence |
|---|---|---|
| SEQ ID NO:65 | $A\beta_{1-42}$ | DAEFRHDSGYEVHHQKLVFFAEDVGSNK GAIIGLMVGGVVIA |
| SEQ ID NO:66 | $A\beta_{1-28}$ | DAEFRHDSGYEVHHQKLVFFAEDVGSNK |
| SEQ ID NO:67 | $A\beta_{1-14}$ | DAEFRHDSGYEVHH |
| SEQ ID NO:68 | $A\beta_{1-12}$ | DAEFRHDSGYEV |
| SEQ ID NO:69 | $A\beta_{1-10}$ | DAEFRHDSGY |

TABLE 4

| Immunogen | Amino Acid Sequence | SEQ ID NO |
|---|---|---|
| A$\beta_{1-28}$-GG-HBV Th | DAEFRHDSGYEVHHQKLVFFAEDVGSNK-GG-FFLLTRILTIPQSLD | 70 |
| A$\beta_{1-10}$-εK-IS-MVF Th1-16 | DAEFRHDSGY-εK-ISITEIKGVIVHRIETILF | 71 |
| A$\beta_{1-12}$-K-IS-MVF Th1-16 | DAEFRHDSGYEV-εK-ISITEIKGVIVHRIETILF | 72 |
| A$\beta_{1-14}$-εK-IS-MVF Th1-16 | DAEFRHDSGYEVHH-εK-ISITEIKGVIVHRIETILF | 73 |
| A$\beta_{1-28}$-εK-IS-MVF Th1-16 | DAEFRHDSGYEVHHQKLVFFAEDVGSNK-εK-ISITEIKGVIVHRIETILF | 74 |
| A$\beta_{1-14}$-εK-MVF | DAEFRHDSGYEVHH-εK-ISISEIKGVIVHKIEGILF | 75 |
| Th1-9 | T RT TR T | 76 |

TABLE 5

| | | | ELISA Titer ($Log_{10}$) | | | | | | | |
|---|---|---|---|---|---|---|---|---|---|---|
| | | | 4 WPI | | | | 6 WPI | | | |
| Immunogen | Adjuvant | GP ID # | A$\beta_{1-14}$ | Avg. | A$\beta_{1-42}$ | Avg. | A$\beta_{1-14}$ | Avg. | A$\beta_{1-42}$ | Avg. |
| A$\beta_{1-28}$ | Alum | 1630 | 1.244 | 2.326 | 0.878 | 2.401 | 0.888 | 1.966 | 1.202 | 2.405 |
| (SEQ ID NO: 66) | | 1631 | 3.408 | | 3.924 | | 3.044 | | 3.608 | |
| A$\beta_{1-42}$ | Alum | 1634 | 0.773 | 1.124 | 0.680 | 1.461 | 1.062 | 1.784 | 1.203 | 1.807 |
| (SEQ ID NO: 65) | | 1635 | 1.474 | | 2.242 | | 2.505 | | 2.510 | |

TABLE 6

| | | | ELISA Titer ($Log_{10}$) | | | | | | | |
|---|---|---|---|---|---|---|---|---|---|---|
| | | GP | 4 WPI | | | | 6 WPI | | | |
| Immunogen | Adjuvant | ID # | A$\beta_{1-14}$ | Avg. | A$\beta_{1-42}$ | Avg. | A$\beta_{1-14}$ | Avg. | A$\beta_{1-42}$ | Avg. |
| A$\beta_{1-14}$ | ISA 51 | 1658 | 1.168 | 1.129 | 1.229 | 0.975 | 1.100 | 1.271 | 1.285 | 1.080 |
| (SEQ ID NO: 67) | | 1659 | 1.090 | | 0.720 | | 1.441 | | 0.874 | |
| A$\beta_{1-28}$ | ISA51 | 1632 | 2.341 | 2.291 | 3.656 | 3.382 | 2.276 | 2.715 | 3.359 | 3.455 |
| (SEQ ID NO: 66) | | 1633 | 2.241 | | 3.107 | | 3.153 | | 3.550 | |
| A$\beta_{1-28}$-GG-HBVTh | ISA51 | 1642 | 4.792 | 4.612 | 4.526 | 4.582 | 4.548 | 4.498 | 4.441 | 4.261 |
| (SEQ ID NO: 70) | | 1643 | 4.432 | | 4.637 | | 4.447 | | 4.081 | |
| A$\beta_{1-42}$ | ISA51 | 1636 | 2.724 | 1.864 | 3.603 | 2.402 | 2.286 | 1.997 | 3.250 | 2.873 |
| (SEQ ID NO: 65) | | 1637 | 1.004 | | 1.201 | | 1.707 | | 2.495 | |

TABLE 7

| | | | ELISA Titer ($Log_{10}$) | | | | | | | |
|---|---|---|---|---|---|---|---|---|---|---|
| | | | 4 WPI | | | | 6 WPI | | | |
| Immunogen | Adjuvant | GP ID # | A$\beta_{1-14}$ | Avg. | A$\beta_{1-42}$ | Avg. | A$\beta_{1-14}$ | Avg. | A$\beta_{1-42}$ | Avg. |
| A$\beta_{1-10}$-εK-MVF | CFA/IFA | 1666 | 4.293 | 4.495 | 4.924 | 5.087 | 4.414 | 4.320 | 5.180 | 5.265 |
| Th1-16 | | 1667 | 4.696 | | 5.250 | | 4.225 | | 5.350 | |
| (SEQ ID NO: 71) | | | | | | | | | | |
| A$\beta_{1-12}$-εK-MVF | CFA/IFA | 1664 | 4.577 | 4.495 | 5.100 | 4.891 | 5.320 | 4.545 | 6.000 | 5.278 |
| Th1-16 | | 1665 | 4.322 | | 4.682 | | 3.700 | | 4.555 | |
| (SEQ ID NO: 72) | | | | | | | | | | |
| A$\beta_{1-14}$-εK-MVF | CFA/IFA | 1660 | 3.700 | 3.285 | 4.677 | 5.060 | 4.544 | 4.683 | 5.250 | 5.625 |
| Th1-16 | | 1661 | 4.764 | | 5.443 | | 4.822 | | 6.000 | |
| (SEQ ID NO: 73) | | | | | | | | | | |
| A$\beta_{1-28}$-εK-MVF | CFA/IFA | 1584 | 3.355 | 3.201 | 4.610 | 4.328 | 2.743 | 3.592 | 4.487 | 4.901 |
| Th1-16 | | 1585 | 3.707 | | 4.688 | | 3.731 | | 5.155 | |
| (SEQ ID NO: 74) | | 1586 | 2.545 | | 3.685 | | 4.304 | | 5.061 | |

TABLE 8

| | | | ELISA Titer ($Log_{10}$) | | | | | | | |
|---|---|---|---|---|---|---|---|---|---|---|
| | | | 4 WPI | | | | 6 WPI | | | |
| Immunogen | Adjuvant | GP ID # | $A\beta_{1-42}$ | Avg. | Th peptide or KLH | Avg | $A\beta_{1-42}$ | Avg. | Th peptide or KLH | Avg |
| $A\beta_{1-14}$ | ISA 51 | 1658 | 1.229 | 0.975 | NA | NA | 1.285 | 1.080 | NA | NA |
| (SEQ ID NO: 67) | | 1659 | 0.720 | | NA | | 0.874 | | NA | |
| $A\beta_{1-14}$-εK-MVF | ISA 51 | 1662 | 4.388 | 4.094 | 0.006 | 0.038 | 4.559 | 4.126 | 0.065 | 0.064 |
| Th1-16 | | 1663 | 3.800 | | 0.070 | | 3.693 | | 0.063 | |
| (SEQ ID NO: 73) | | | | | | | | | | |
| KLH-(C) $A\beta_{1-14}$ | ISA 51 | 1670 | 3.181 | 3.342 | 4.672 | 4.903 | 2.625 | 2.736 | 4.876 | 5.018 |
| (SEQ ID NO: 67) | | 1671 | 3.502 | | 5.133 | | 2.846 | | 5.160 | |

TABLE 9

| | | ELISA Titer ($Log_{10}$) | | | | Immunostaining[a] of serial frozen sections of AD's brain tissue | |
|---|---|---|---|---|---|---|---|
| | GP | $A\beta_{1-42}$ | | $A\beta_{1-14}$ | | | |
| Vaccine Formulation | ID# | | Avg | | Avg | Plaque | TSBV |
| $A\beta_{1-28}$ in Alum | 1630 | 0.878 | 2.401 | 1.244 | 2.326 | +1 | +4 |
| | 1631 | 3.924 | | 3.408 | | | |
| $A\beta_{1-28}$ in ISA51 | 1632 | 3.686 | 3.397 | 2.341 | 2.291 | +3 | +5 |
| | 1633 | 3.107 | | 2.241 | | | |
| $A\beta_{1-28}$-εK-MVF Th1-16 in CFA/IFA | 1584 | 4.610 | 4.328 | 3.355 | 3.201 | +4 | +6 |
| (SEQ ID NO: 74) | 1585 | 4.688 | | 3.707 | | | |
| | 1586 | 3.685 | | 2.540 | | | |
| $A\beta_{1-28}$-εK-MVF Th1-16 in ISA51 | 1642 | 3.603 | 4.582 | 2.724 | 3.510 | +4 | +6 |
| (SEQ ID NO: 74) | 1643 | 1.201 | | 1.004 | | | |
| $A\beta_{1-14}$ in ISA51 | 1658 | 1.229 | 0.975 | 1.168 | 1.129 | Neg | Neg |
| | 1659 | 0.720 | | 1.090 | | | |
| $A\beta_{1-14}$-εK-MVF Th1-16 in CFA/IFA | 1660 | 4.677 | 5.060 | 3.700 | 4.232 | +4 | +6 |
| (SEQ ID NO: 73) | 1661 | 5.443 | | 4.764 | | | |
| $A\beta_{1-14}$-εK-MVF Th1-16 in ISA51 | 1662 | 4.388 | 4.094 | 3.551 | 3.285 | +4 | +6 |
| (SEQ ID NO: 73) | 1663 | 3.800 | | 3.018 | | | |
| $A\beta_{1-12}$-εK-MVF Th1-16 in CFA/IFA | 1664 | 5.100 | 4.891 | 4.577 | 4.450 | +4 | +6 |
| (SEQ ID NO: 72) | 1665 | 4.682 | | 4.322 | | | |
| $A\beta_{1-10}$-εK-MVF Th1-16 in CFA/IFA | 1666 | 4.924 | 5.087 | 4.293 | 4.455 | +4 | +5 |
| (SEQ ID NO: 71) | 1667 | 5.250 | | 4.696 | | | |
| KLH-(C) $A\beta_{1-14}$ in ISA51 | 1670 | 3.181 | 3.342 | 3.280 | 3.102 | +2 | +4 |
| | 1635 | 3.502 | | 2.924 | | | |
| Negative Control (preimmune serum) | | <0.5 | | <0.5 | | Neg | Neg |

[a]Serial dilution @ 1:100

TABLE 10

| | | | ELISA Titer ($Log_{10}$) | | | | | | Immunostaining of frozen sections of AD brain (8 wpi) | |
|---|---|---|---|---|---|---|---|---|---|---|
| | | | $A\beta_{1-42}$ | | | $A\beta_{1-14}$ | | | | |
| Group # | Vaccine Formulation | Dose | 0 WPI | 5 WPI | 8 WPI | 0 WPI | 5 WPI | 8WPI | Plaques | TSBV |
| 1 | $A\beta_{1-28}$-εKV-MVF Th1-16 | 25 μg | 0.894 | 2.962 | 2.736 | 0.665 | 1.745 | 2.706 | +2 | + |
| 2 | in ISA51 | 100 μg | 0.610 | 2.987 | 3.640 | 0.794 | 2.816 | 4.800 | +4 | +6 |
| 3 | (SEQ ID NO: 74) | 400 μg | 0.696 | 2.696 | 4.050 | 0.539 | 4.250 | 3.799 | +4 | +6 |
| 4 | $A\beta_{1-28}$ + $A\beta_{1-42}$ in Alum | 100 μg | 0.897 | 1.963 | 2.485 | 0.798 | 0.727 | 2.850 | + | + |
| 5 | Negative control | — | — | — | — | — | — | — | Neg | Neg |

The invention claimed is:

1. A peptide immunogen comprising:

(i) a promiscuous helper T cell (Th) epitope of SEQ ID NO: 1;

(ii) said promiscuous Th epitope being conjugated to an N-terminal fragment of $A\beta_{1-42}$ peptide consisting of SEQ ID NO: 67, and (iii) optionally said promiscuous Th epitope is conjugated to the N-terminal fragment of $A\beta_{1-42}$ peptide by means of a spacer consisting of at least an amino acid to separate the Th epitope from the N-terminal fragment of $A\beta_{1-42}$ peptide.

2. The peptide immunogen of claim 1, wherein the spacer is selected from the group consisting of an amino acid, Gly-Gly, ϵ-N-Lys, and Pro-Pro-Xaa-Pro-Xaa-Pro (SEQ ID NO:77).

3. The peptide immunogen of claim 1, wherein the spacer is ϵ-N-Lys.

4. A peptide immunogen comprising the following formula:

(A)n-(SEQ ID NO: 67)-(B)o-(Th)m-X; or (A)n-(Th)m-(B)o-(SEQ ID NO: 67)-X; wherein each A is independently an amino acid;

each B is a spacer selected from the group consisting of an amino acid, Gly-Gly, ϵ-N-Lys, and Pro-Pro-Xaa-Pro-Xaa-Pro (SEQ ID NO:77);

Th comprise an amino acid sequence that constitutes a promiscuous helper T cell epitope SEQ ID NO: 1;

X is an $\alpha$-COOH or $\alpha$-$CONH_2$ of an amino acid;

n is 0 to 10;

m is 1 to 4; and o is 0 to 10.

5. The peptide immunogen of claim 4, wherein the spacer is ϵ-N-Lys.

6. A composition comprising the peptide immunogen of claim 1 and a pharmaceutically acceptable adjuvant and/or carrier selected from the group consisting of alum, liposyn, saponin, squalene, L121, emulsigen monophosphyryl lipid A (MPL), polysorbate 80, QS21, Montanide ISA51, ISA35, ISA206 and ISA 720.

7. A composition comprising the peptide immunogen of claim 2 and a pharmaceutically acceptable adjuvant and/or carrier selected from the group consisting of alum, liposyn, saponin, squalene, L121, emulsigen monophosphyryl lipid A (MPL), polysorbate 80, QS21, Montanide ISA51, ISA35, ISA206 and ISA 720.

8. A composition comprising the peptide immunogen of claim 3 and a pharmaceutically acceptable adjuvant and/or carrier selected from the group consisting of alum, liposyn, saponin, squalene, L121, emulsigen monophosphyryl lipid A (MPL), polysorbate 80, QS21, Montanide ISA51, ISA35, ISA206 and ISA 720.

9. A composition comprising the peptide immunogen of claim 4 and a pharmaceutically acceptable adjuvant and/or carrier selected from the group consisting of alum, liposyn, saponin, squalene, L121, emulsigen monophosphyryl lipid A (MPL), polysorbate 80, QS21, Montanide ISA51, ISA35, ISA206 and ISA 720.

10. A composition comprising the peptide immunogen of claim 5 and a pharmaceutically acceptable adjuvant and/or carrier selected from the group consisting of alum, liposyn, saponin, squalene, L121, emulsigen monophosphyryl lipid A (MPL), polysorbate 80, QS21, Montanide ISA51, ISA35, ISA206 and ISA 720.

* * * * *